United States Patent
Javet et al.

(10) Patent No.: US 7,374,583 B2
(45) Date of Patent: *May 20, 2008

(54) CATIONIC AZACYANINE DYES AND COLORING AGENTS CONTAINING SAID DYES

(75) Inventors: Manuela Javet, Marly (CH); Catherine Müller, Marly (CH)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/732,214

(22) Filed: Apr. 3, 2007

(65) Prior Publication Data

US 2007/0220685 A1    Sep. 27, 2007

(51) Int. Cl.
*A61K 7/13* (2006.01)
(52) U.S. Cl. ............... 8/405; 8/406; 8/429; 8/431; 8/688; 8/689; 8/690; 8/691; 548/100
(58) Field of Classification Search ............... 8/405, 8/406, 429, 431, 688, 689, 690, 691; 548/100
See application file for complete search history.

(56) References Cited

FOREIGN PATENT DOCUMENTS

| DE | 3929383 A1 | 3/1991 |
|---|---|---|
| DE | 19618595 A1 | 11/1997 |
| JP | 07085499 A | 3/1995 |
| JP | 07126543 A | 5/1995 |

OTHER PUBLICATIONS

STIC Search Report dated Sep. 20, 2007.*
Rosetti, Monica et al., "Reactions of benzoyl chloride-activated 1-methyl-2-phenyl-3-nitrosoindole with indole and indolizine derivatives as nucleophiles: a case of 1,3-migration," *Journal of Chemical Research, Synposes*, Nr. 6, 1999, pp. 362-363, XP009059148.

Siemeling, Ulrich et al., "Large scale synthesis of 4'-(4-bromophenyl)-2,2':61,2'-terpyridine and nature of the mysterious green by-product," *Zeitschrift Fuer Naturforschung, B: Chemical Sciences*, Bd. 58, Nr. 5, 2003, pp. 443-446, XP009059229.
Kröck, Friedrich W. et al., "Novel cyanines. 9. New indolizinc synthesis with 2-acylpyridines. II. Blue azacyanines," *Chemische Berichte*, Bd. 104, Nr. 5, 1971, pp. 1645-1654, XP009059227.
Lucedio Greci et al., "Nitrenium ions. Reactions of N,N-dimethyl-p-benzoyloxyaniline-iminium chloride with indoles and indolizines. X-ray structure of unexpected [2-chloro-4-(4-dimethylaminophenyl-ONN-azoxy)-phenyl]dimethylamine (azoxy derivative)," *Organic & Biomolecular Chemistry*, Bd. 1, Nr. 21, 2003, pp. 3768-3771, XP002360345.
International Search Report for PCT/EP2005/010322, Jan. 16, 2006 (5 pages).
Kröck, Friedrich W. et al., "Novel cyanines. 9. New indolizine synthesis with 2-acylpyridines. II. Blue azacyanines," *Chemische Berichte*, Bd. 104, Nr. 5, 1971, pp. 1645-1654, XP009059227.

* cited by examiner

*Primary Examiner*—Eisa Elhilo
(74) *Attorney, Agent, or Firm*—Idris N. McKelvey

(57) ABSTRACT

The present invention relates to agents containing cationic azacyanine dyes having formula (I) for dyeing fibers, such as, for example, keratin fibers, wool, silk or fleeces, and in particular human hair, as well as to new asymmetrical azacyanine dyes.

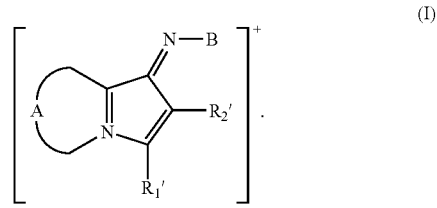

(I)

12 Claims, No Drawings

CATIONIC AZACYANINE DYES AND COLORING AGENTS CONTAINING SAID DYES

FIELD OF INVENTION

The present invention relates to agents containing cationic azacyanine dyes for dyeing fibers, such as keratin fibers, wool, silk, or fleeces, and in particular human hair, as well as new azacyanine dyes.

BACKGROUND OF THE INVENTION

Cationic direct-penetrating dyes have long been known in hair tinting products. In oxidative dyeing systems, which during the dyeing process simultaneously lighten the natural hair melanin, in particular nitro and azo dyes are used, because most other types of dyes cannot withstand the oxidation process.

It is known to use particular azacyanines for the surface treatment of optical recording media.

Surprisingly, it has been discovered that particular cationic azacyanine dyes enable coloring to be carried out into the blue and blue-green ranges, and that, depending on the substitution pattern, they are oxidation-stable and can thus also be used in oxidative dyeing systems.

SUMMARY OF THE INVENTION

The subject matter of the present invention is therefore:

(a) an agent for the non-oxidative dyeing of fibers, preferably keratin fibers and in particular human hair, wherein it contains at least one cationic azacyanine dye having the general formula (I);

(b) an agent for the simultaneous lightening and dyeing of fibers, preferably keratin fibers, and in particular human hair, that contains, besides the dye having formula (I) an oxidizing agent, and wherein it contains at least one cationic azacyanine dye having the general formula (I) that is stable in relation to oxidizing agents; and (c) an oxidative coloring agent for dyeing fibers, preferably keratin fibers and in particular human hair, on the basis of at least one oxidative dye precursor, wherein it contains at least one cationic azacyanine dye having the general formula (I) that is stable in relation to oxidizing agents;

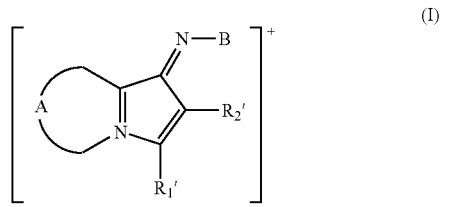
(I)

"A" represents the formation of an aromatic carbocyclic or heterocyclic (nitrogen, oxygen, or sulfur, possibly containing up to two additional heteroatoms in addition to the bridge nitrogen) 5- or 6-ring required group;

"R1'" is equal to an unbranched or branched (C1-C10) alkyl chain that can be substituted with one or more alkoxy groups, hydroxyl groups, carboxylic acid amide groups, dialkyl amino groups, alkyl amino groups, carboxylic acid ester groups, carboxylic acid groups, or sulfonic acid groups, an unsubstituted benzyl group, a benzyl group substituted with one or more alkyl groups, alkoxy groups, alkoxyalkyl groups, hydroxyl groups, hydroxyalkyl groups, carboxylic acid amide groups, dialkylamine groups, carboxylic acid ester groups, alkyl carboxylic acid ester groups, carboxylic acid groups, alkylcarboxylic acid groups, sulfonic acid groups or halogen atoms (F, Cl, Br, I) or with a six-member or five-member aromatic carbocyclic or heterocyclic (nitrogen, oxygen, or sulfur) ring that can be unsubstituted or substituted with one or more alkyl groups, alkoxy groups, alkoxyalkyl groups, hydroxyl groups, hydroxyalkyl groups, carboxylic acid amide groups, dialkyl amine groups, carboxylic acid ester groups, alkylcarboxylic acid ester groups, carboxylic acid groups, alkylcarboxylic acid groups, sulfonic acid groups or halogen atoms (F, Cl, Br, I);

"R2'" represents hydrogen, an alkyl group, a hydroxyalkyl group, an alkoxyalkyl group, an alkoxy group, a halogen atom (F, Cl, Br, I), or a six-member or five-member aromatic carbocyclic or heterocyclic (nitrogen, oxygen, or sulfur) ring that can be unsubstituted or substituted with an alkyl group, an alkoxy group, an alkoxyalkyl group, a hydroxyl group, a hydroxy alkyl group, an alkylcarboxylic acid amide group, a dialkylamino group, a carboxylic acid ester group, an alkylcarboxylic acid ester group, a carboxylic acid group, an alkylcarboxylic acid group, a sulfonic acid group, an alkylsulfonic acid group, an unsubstituted or substituted benzyl group, or a halogen atom (F, Cl, Br, I); and "B" represents an aromatic molecule part with tertiary nitrogen.

The following compounds, having formulas (Ia) to (Ie), can, for example, be named as suitable compounds having formula (I), the residues "R1'," "R2'," and B having the significance stated above, and "R3'" is equal to hydrogen, an alkyl group, an alkoxy group, an alkoxyalkyl group, a hydroxyl group, a hydroxyalkyl group, an alkylcarboxylic acid amide group, an amino group, an alkylamino group, a dialkylamino group, a carboxylic acid ester group, an alkylcarboxylic acid ester group, a carboxylic acid group, an alkylcarboxylic acid group, a sulfonic acid group, an alkylsulfonic acid group, or a halogen atom (F, Cl, Br, I);

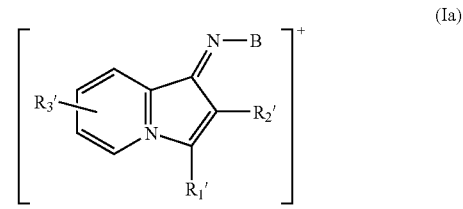
(Ia)

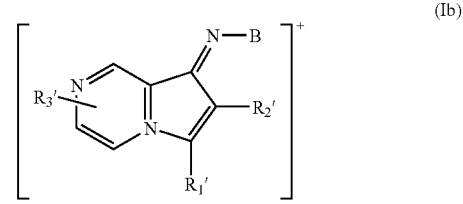
(Ib)

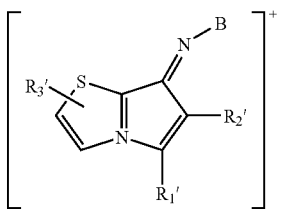 (Ic)

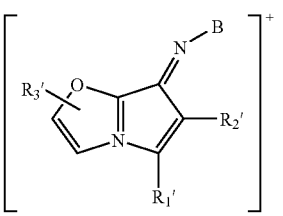 (Id)

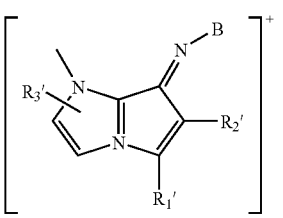 (Ie)

As residue groups "B" substituted indoles, indazoles, indolizines, pyrrolo[1,2-a]pyrazines, pyrrolo[2,1-b][1,3]thiazoles, pyrrolo[2,1-b][1,3]oxazoles, pyrrolo[1,2-a]imidazoles, pyrazoles, paraphenylenamines, imidazoles, pyrroles and pyrazolin-5-ones having formulas (If) bis(Ir) are suitable;

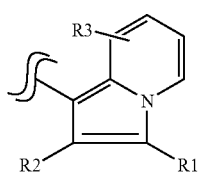 (If)

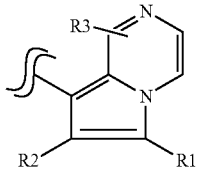 (Ig)

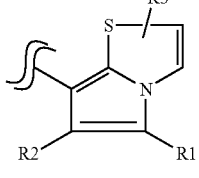 (Ih)

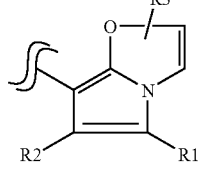 (Ii)

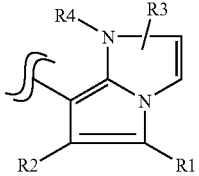 (Ik)

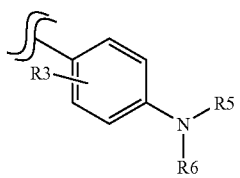 (Il)

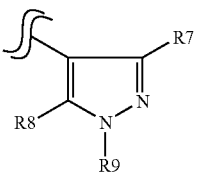 (Im)

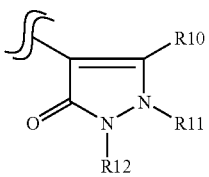 (In)

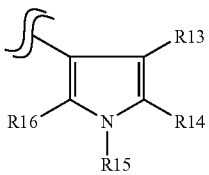 (Io)

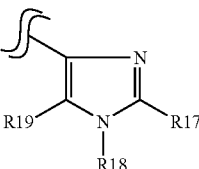 (Ip)

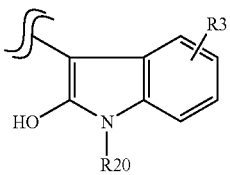 (Iq)

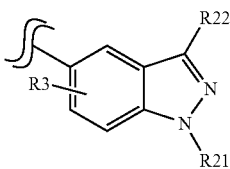 (Ir)

the residues "R1" being equal to an unbranched or branched (C1-C10) alkyl chain that can be substituted with one or more alkoxy groups, hydroxyl groups, carboxylic acid amide groups, dialkylamino groups, alkylamino groups, carboxylic acid ester groups, carboxylic acid groups or sulfonic acid groups, an unsubstituted benzyl group, a benzyl group substituted with one or more alkyl groups, alkoxy groups, alkoxyalkyl groups, hydroxyl groups, hydroxyalkyl groups, carboxylic acid amide groups, dialkylamine groups, carboxylic acid ester groups, alkylcarboxylic acid ester groups, carboxylic acid groups, alkylcarboxylic acid groups, sulfonic acid groups or halogen atoms (F, Cl, Br, I), or a six-member or five-member aromatic carbocyclic or heterocyclic (nitrogen, oxygen, or sulfur) ring, that can be unsubstituted or substituted with one or more alkyl groups, alkoxy groups, alkoxyalkyl groups, hydroxyl groups, hydroxyalkyl groups, carboxylic acid amide groups, dialkylamine groups, carboxylic acid ester groups, alkylcarboxylic acid ester groups, carboxylic acid groups, alkylcarboxylic acid groups, sulfonic acid groups or halogen atoms (F, Cl, Br, I); and "R2" meaning hydrogen, an alkyl group, a hydroxyalkyl group, an alkoxyalkyl group, an alkoxy group, a halogen atom (F, Cl, Br, J), or a six-member or five-member aromatic carbocyclic or heterocyclic (nitrogen, oxygen or sulfur) ring that can be unsubstituted or substituted with an alkyl group, an alkoxy group, an alkoxyalkyl group, a hydroxyl group, a hydroxyalkyl group, an alkylcarboxylic acid amide group, a dialkylamino group, a carboxylic acid ester group, an alkylcarboxylic acid ester group, a carboxylic acid group, an alkylcarboxylic acid group, a sulfonic acid group, an alkylsulfonic acid group, an unsubstituted or substituted benzyl group or a halogen atom (F, Cl, Br, I).

R3 is equal to hydrogen, an alkyl group, an alkoxy group, an alkoxyalkyl group, a hydroxyl group, a hydroxyalkyl group, an alkylcarboxylic acid amide group, an amino group, an alkylamino group, a dialkylamino group, a carboxylic acid ester group, an alkylcarboxylic acid ester group, a carboxylic acid group, an alkylcarboxylic acid group, a sulfonic acid group, an alkylsulfonic acid group or a halogen atom (F, Cl, Br, I); the residues R4, R5, R6, R9, R11, R12, R15, R18, R20, and R21 being, independent of one another, equal to an unbranched or branched (C1-C10) alkyl chain that can be unsubstituted or substituted with an alkoxy group, a hydroxyl group, a carboxylic acid amide group, a dialkylamino group, an alkylamino group, a carboxylic acid ester group, a carboxylic acid group or a sulfonic acid group, an unsubstituted benzyl group, a benzyl group substituted with an alkyl group, an alkoxy group, an alkoxyalkyl group, a hydroxyl group, a hydroxyalkyl group, a carboxylic acid amide group, a dialkylamino group, a carboxylic acid ester group, an alkylcarboxylic acid ester group, a carboxylic acid group, an alkylcarboxylic acid group, a sulfonic acid group or a halogen atom (F, Cl, Br, I), or with a six-member or five-member aromatic carbocyclic or heterocyclic (nitrogen, oxygen or sulfur) ring that can be unsubstituted or substituted with an alkyl group, an alkoxy group, an alkoxyalkyl group, a hydroxyl group, a hydroxyalkyl group, a carboxylic acid amide group, a dialkylamino group, a carboxylic acid ester group, an alkylcarboxylic acid ester group, a carboxylic acid group, an alkylcarboxylic acid group, a sulfonic acid group or a halogen atom (F, Cl, Br, I); and R7, R8, R10, R13, R14, R16, R17, R19, and R22 are independent of one another, equal to hydrogen, an unbranched or branched (C1-C10) alkyl chain that can be unsubstituted or substituted with an alkoxy group, a hydroxyl group, a carboxylic acid amide group, a dialkylamine group, an alkylamine group, a carboxylic acid ester group, a carboxylic acid group or a sulfonic acid group, an unsubstituted benzyl group, a benzyl group substituted with an alkyl group, an alkoxy group, an alkoxyalkyl group, a hydroxyl group, a hydroxyalkyl group, a carboxylic acid amide group, a dialkylamino group, a carboxylic acid ester group, an alkylcarboxylic acid ester group, a carboxylic acid group, an alkylcarboxylic acid group, a sulfonic acid group, or a halogen atom (F, Cl, Br, I), a hydroxyl group, an amino group, an alkoxy group, a substituted phenyloxy group, a dialkylamino group, a substituted benzylamino group, a substituted phenylamino group, an alkylamino group or with a six-member or five-member aromatic carbocyclic or heterocyclic (nitrogen, oxygen, or sulfur) ring that can be unsubstituted or substituted with an alkyl group, an alkoxy group, an alkoxyalkyl group, a hydroxyl group, a hydroxyalkyl group, a carboxylic acid amide group, a dialkylamine group, a carboxylic acid ester group, an alkylcarboxylic acid ester group, a carboxylic acid group, an alkylcarboxylic acid group, a sulfonic acid group or a halogen atom (F, Cl, Br, I).

The symmetrical azacyanines, in which the two ring systems situated at the N atom are identical (e.g., azacyanines having formula (II)), can be created using the method of F. W. Kröck and F. Kröhnke, Chem. Ber. 104, 1645-1654 (1971). In this method, one starts with an aromatic nitrogen compound having an alpha-keto-alkyl chain in position 2, e.g., 2-acetylpyridine, that is converted in synthesis stage 1 under alkaline conditions with an aromatic aldehyde, and then couples with itself in a second stage in the presence of ammonium acetate/glacial acetic acid to form the dye. Asymmetrical dyes (i.e., compounds having formula (I), in which the two ring systems situated at the N atom are not identical, e.g., the following compounds having formulas (III) to (VII)), are created in the second stage through reaction with a primary amine (without the addition of an ammonium compound), or with the addition of an ammonium compound, with a ketone or aldehyde.

Symmetrical dyes according to the present invention can, for example, have the following mesomeric basic structure (II),

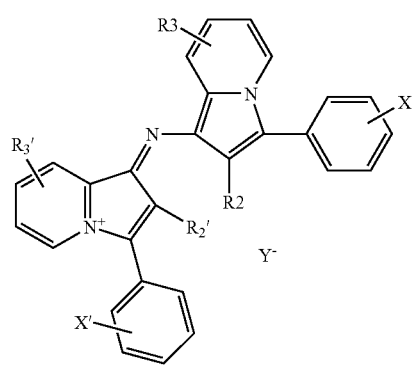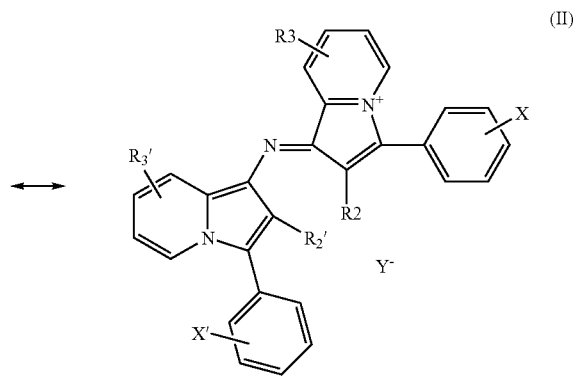

the residues "R2," "R2'," "R3," and "R3" having the meaning indicated above (with "R2"="R2'," "R3"="R3'"), "X" and "X'" being identical and representing hydrogen, an alkyl group, an alkoxy group, an alkoxyalkyl group, a hydroxyl group, a hydroxyalkyl group, an alkylcarboxylic acid amide group, a dialkylamino group, a carboxylic acid ester group, an alkylcarboxylic acid ester group, a carboxylic acid group, an alkylcarboxylic acid group, a sulfonic acid group, an alkylsulfonic acid group or a halogen atom, and "Y" meaning a counter ion from the group of the organic or inorganic acid anions, such as, e.g., halides (chloride, bromide, iodide), sulfates, acetates, lactates, perchlorate or hexafluorophosphate. (In the following text, of the two mesomeric structures only the one on the left will be used for the purpose of illustration).

With "R2"="R2'"="R3"="R3'"="H," "X"="X'"=4-methoxy and "Y" =acetate, for example, a dye (IIa) is obtained that penetrates bleached hair with a deep blue color. Depending on the substitution pattern of the dyes, dyeings are also possible in the presence of hydrogen peroxide/alkalizing agents, and even persulfates.

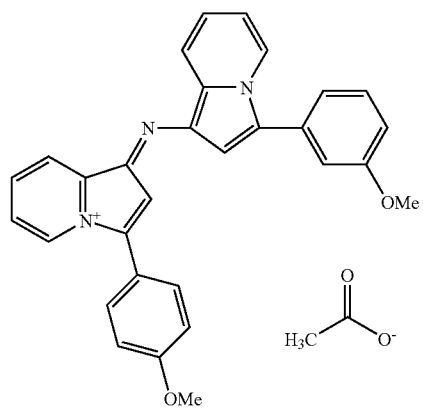

(IIa)

With the use of asymmetrical azacyanines, such as, e.g., dye (III) or (IV), in the second stage an aromatic amine is to be added instead of ammonium acetate. In this way, with 4,5-diamin-pyrazoles as reaction partners, brilliant color tones in the violet range result.

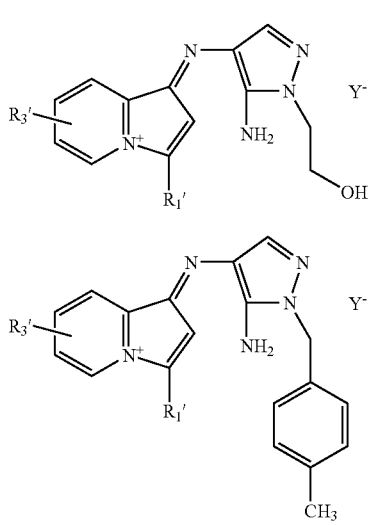

(III)

(IV)

With "R1'"=4-methoxyphenyl, "R3'"=hydrogen and "Y"=acetate, an intensively violet-red dye is obtained. Compound (III) is practically not resistant to hydrogen peroxide/alkalizing agents, and compound (IV) has only limited resistance thereto.

A changed substitution pattern at nitrogen in position 5 of the pyrazole significantly increases the peroxide stability.

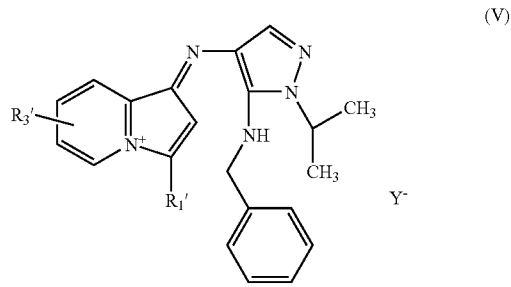

(V)

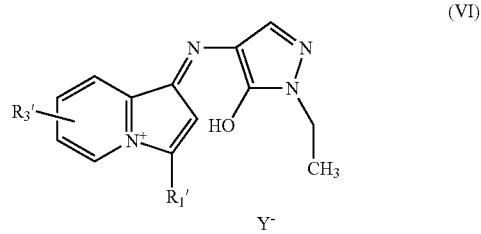

(VI)

With "R1'"=4-methoxyphenyl, "R3'"=hydrogen and "Y"=acetate, brilliant violet-red dyes are obtained, dye (V) being largely resistant to hydrogen peroxide/alkalizing agents, and dye (VI) being very resistant thereto.

If in the second synthesis stage a pyrazolin-5-on-amine is used as the coupling partner, then, e.g., with 4-aminoantipyrine a brilliant red dye is obtained ("R1'"=4-methoxyphenyl, "R3'"=hydrogen and "Y"=acetate) of formula (VII).

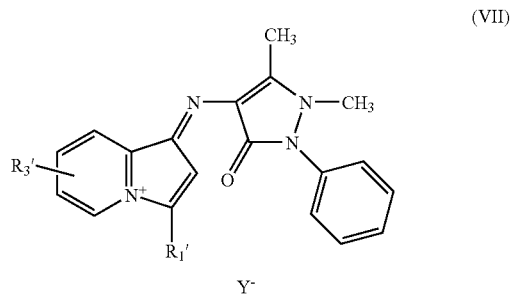

(VII)

The residue "R1'" or "R1" is preferably introduced with the aldehydes vanillin (4-hydroxy-3-methoxybenzaldehyde), isovanillin (3-hydroxy-4-methoxy-benzaldehyde), 3,4-dihydroxy-benzaldehyde, 4-hydroxybenzaldehyde, 3,5-dimethoxy-4-hydroxy-benzaldehyde, 4-dimethylaminobenzaldehyde, 4-methyl-5-imidazole-carboxaldehyde, 4-methoxybenzaldehyde, 4-dimethylamino-zimtaldehyde, 4-hydroxy-2-methoxy-benzaldehyde, 3,5-dimethyl-4-hydroxybenzaldehyde, 4-dimethylamino-2-methoxybenzaldehyde, 2-hydroxybenzaldehyde, 4-hydroxy-1-naphthaldehyde, 4-methoxy-1-naphthaldehyde, 4-dimethyl-amino-1- naphthaldehyde, 4'-hydroxy-biphenyl-1-carbaldehyde, 2-hydroxy-3-methoxybenzaldehyde, 2,4-dihydroxybenzaldehyde, 3,4-dihydroxybenzaldehyde, 2,5-dihydroxybenzaldehyde, 2,3,4-trihydroxybenzaldehyde, 3,4,5-trihydroxybenzaldehyde, 2,4,6-trihydroxybenzaldehyde, 2,4-dimethoxybenzaldehyde, 2,3-dimethoxybenzaldehyde, 2,5-dimethoxybenzaldehyde, 3,5-dimethoxybenzaldehyde, 3,4-dimethoxybenzaldehyde, indole-3-carbaldehyde, benzene-1,4-dicarbaldehyde, 4-ethoxybenzaldehyde, 2-methyl-1,4-naphthoquinone, 4-carboxybenzaldehyde, 4-hydroxy-3-methoxyzimtaldehyde, 3,5-dimethoxy-4-hydroxy-zimtaldehyde, 3-methoxy-4-(1-pyrrolidinyl)-benzaldehyde, 4-diethylamino-3-methoxybenzaldehyde, 1,2-phthaldialdehyde, pyrrol-2-aldehyde, thiophen-2-aldehyde, thiophen-3-aldehyde, chromone-3-carboxaldehyde, 6-methyl-4-oxo-1 (4H)-benzopyran-3-carbaldehyde, N-methylpyrrol-2-aldehyde, 5-methylfurfural, 6-hydroxychromen-3-carboxaldehyde, 6-methylindol-3-carboxaldehyde, 4-dibutyl-aminobenzaldehyde, N-ethylcarbazol-3-aldehyde, 4-diethylamino-2-hydroxybenzaldehyde, 3,4-dimethoxy-5-hydroxybenzaldehyde, 5-(4-(diethylamino)phenyl)-2,4-pentadienal, 2,3-thiophendicarboxaldehyde, 2,5-thiophendicarboxaldehyde, 2-methoxy-1-naphthaldehyde, 3-ethoxy-4-hydroxybenzaldehyde, 2-nitrobenzaldehyde, 3-nitrobenzaldehyde and 4-nitrobenzaldehyde.

In the second stage, possible coupling components include, as described above, self-coupling or a reaction with other ketones, amines or aldehydes. Self-coupling, and in particular the reaction with other ketones or amines, is preferred.

In the case of asymmetrical dye formation, 6-ring aromates with extracyclic nitrogen, such as the amines or their organic or inorganic salts, are especially preferred coupling partners.

Here, with N,N-bis(2-hydroxyethyl)-p-phenylendiamine the following dye is obtained:

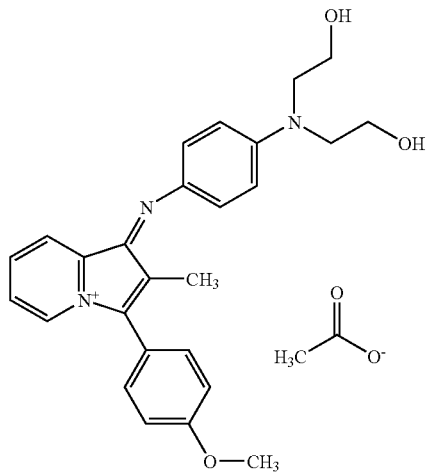

(1E)-1-({4-[bis(2-hydroxyethyl)amino]phenyl}imino)-3-(4-methoxyphenyl)-2-methyl-1H-indoliziniumacetate and, analogously, with N-dimethylamino-p-phenylendiamine, for example, (1E)-1-{[4-(dimethylamino)phenyl]imino}-3-(4-methoxyphenyl)-2-methyl-1H-indolizinium-aceatate [is obtained]

with N-diethylamino-p-phenyldiamine, analogously, for example, (1E)-1-{[4-(diethylamino)phenyl]imino}-3-(4-methoxyphenyl)-2-methyl-1H-indolizinium- acetate [is obtained].

In addition, heterocyclenes containing nitrogen or their organic or inorganic salts, such as, e.g., substituted imidazoles, substituted pyridines, substituted pyrroles, substituted indazoles and substituted pyrazoles are especially preferred.

With 4,5-diamino-1-methyl-1H-pyrazol, the following dye is obtained:

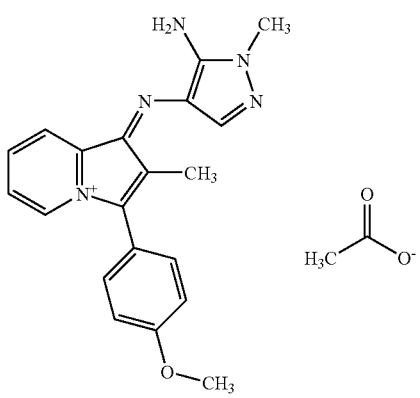

(1E)-1-[(5-amino-1-methyl-1H-pyrazol-4-yl)imino]-3-(4-methoxyphenyl)-2-methyl-1H-indolizinium-acetate.

With 4,5-diamino-1-(4'-methylbenzyl)-pyrazol, the following dye is obtained:

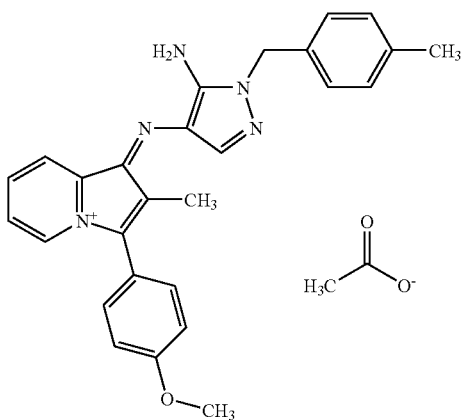

(1E)-1-{[5-amino-1-(4-methylbenzyl)-1H-pyrazol-4-yl] imino}-3-(4-methoxyphenyl)-2-methyl-1H-indolizinium-acetate, and, analogously, with 4,5-diamino-1-(3'-methylbenzyl)-pyrazol, for example, (1E)-1-{[5-amino-1-(3-methylbenzyl)-1H-pyrazol-4-yl] imino}-3-(4-mehtoxypheny)-2-methyl-1H-indolizinium-acetate, and, analogously, with 4,5-diamino-1-(2'-methylbenzyl)-pyrazol, for example, (1E)-1-{[5-amino-1-(4-methylbenzyl)-1H-pyrazol-4-yl] imino}-3-(4-methoxyphenyl)-2-methyl-1H-indolizinium-acetate, and, analogously, with 4,5-diamino-1-(2'-hydroxyethyl)-1H-pyrazol, for example, (1E)-1-{[5-amino-1-(2-hydroxymethyl)-1H-pyrazol-4-yl]imino}-3-(4-methoxypheyl)-2-methyl-1H-indolizinium-acetate, and, analogously, with 4,5-diamino-1-benzyl-1H-pyrazol, for example, (1E)-1-[(5-amino-1-benzyl-1H-pyrazol-4-yl)imino]-3-(4-methoxyphenyl)-2-methyl-1H-indolizinium-acetate.

With 4,5-diamino-1-ethyl-1H-pyrazol, the following dye is obtained:

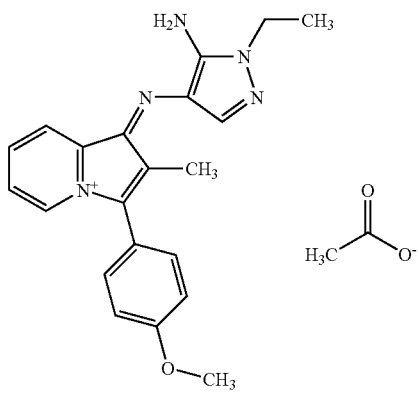

(1E)-1-[(5-amino-1-ethyl-1H-pyrazol-4-yl)imino]-3-(4-methoxyphenyl)-2-methyl-1H-indolizinium-acetate, and, analogously, with 4,5-diamino-1isopropyl-1H-pyrazol, for example, (1E)-1-[(5-amino-1-isopropyl-1H-pyrazol-4-yl)imino]-3-(4-methoxyphenyl)-2-methyl-1H-indolizinium-acetate, and, analogously, with 4,5-diamino-1-pentyl-1H-pyrazol, for example, (1E)-1-[(5-amino-1-pentyl-1H-pyrazol-4-yl)imino]-3-(4-methoxyphenyl)-2-methyland, analogously, with 4,5-diamino-1-(4'-methoxy-benzyl)-1H-pyrazol, for example, (1E)-1-{[5-amino-1-(4-methoxybenzyl)-1H-pyrazol-4-yl]imino}-3-(4-methoxyphenyl)-2-methyl-1H-indolizinium-acetate, and, analogously, with 4,5-diamino-1-(3'-methoxy-benzyl)-1H-pyrazol, for example, (1E)-1-{[5-amino-1-(3-methoxybenzyl)-1H-pyrazol-4-yl]imino}-3-(4-methoxyphenyl)-2-methyl-1H-indolizinium-acetate, and, analogously, with 4,5-diamino-1-(2'-methoxy-benzyl)-1H-pyrazol, for example, (1E)-1-{[5-amino-1-(2-methoxybenzyl)-1H-pyrazol-4-yl]imino}-3-(4-methoxyphenyl)-2-methyl-1H-indolizinium-acetate, and, analogously, with 4,5-diamino-1-(4'-chlorbenzyl)-1H-pyrazol, for example, (1E)-1-{[5-amino-1-(4-chlorbenzyl)-1H-pyrazol-4-yl]imino}-3-(4-methoxyphenyl)-2-methyl-1H-indolizinium-acetate, and, analogously, with 4,5-diamino-1-(3'-chlorbenzyl)-1H-pyrazol, for example, (1E)-1-{[5-amino-1-(3-chlorbenzyl)-1H-pyrazol-4-yl]imino}-3-(4-methoxyphenyl)-2-methyl-1H-indolizinium-acetate, and, analogously, with 4,5-diamino-1-(2'-chlorbenzyl)-1H-pyrazol, for example, (1E)-1-{[5-amino-1-(2-chlorbenzyl)-1H-pyrazol-4-yl]imino}-3-(4-methoxyphenyl)-2-methyl-1H-indolizinium-acetate.

With 4-amino-5-methylamino-1-(4'-methoxybenzyl)-1H-pyrazol, the following dye is obtained:

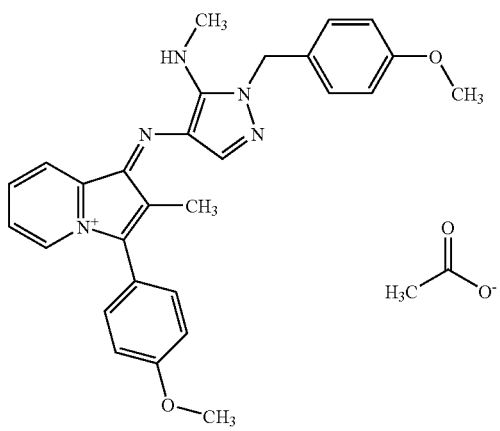

(1E)-1-{[1-(4-methoxybenzyl)-5-(methylamino)-1H-pyrazol-4-yl]imino}-3-(4-methoxyphenyl)-2-methyl-1H-indolizinium-acetate.

With 4-amino-5-(2'-hydroxyethyl)amino-1-(4'-methoxybenzyl)-1H-pyrazol, the following dye is obtained:

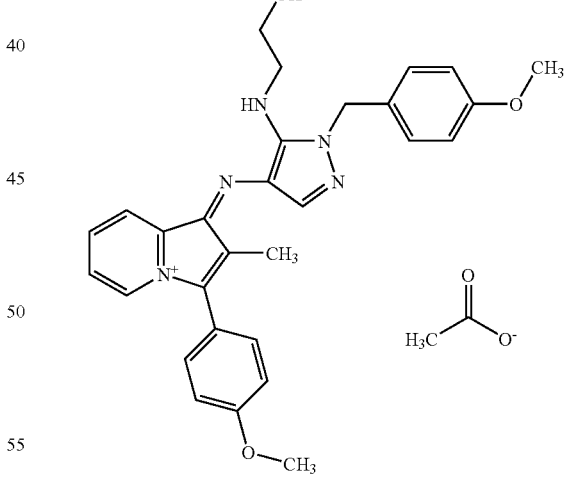

(1E)-1-{[5-[(2-hydroxyethyl)amino]-1-(4-methoxybenzyl)-1H-pyrazol-4-yl]imino}-3-(4-methoxyphenyl)-2-methyl-1H-indolizinium-acetate, and, analogously, with 4-amino-5-methylamino-1-(2'-hydroxyethyl)-1H-pyrazol, for example, (1E)-1-{[1-(2-hydroxyethyl)-5-(methylamino)-1H-pyrazol-4-yl]imino}-3-(4-methoxyphenyl)-2-methyl-1H-indolizinium-acetate.

With 4-amino-1-ethyl-5-hydroxy-1H-pyrazol the following dye is obtained:

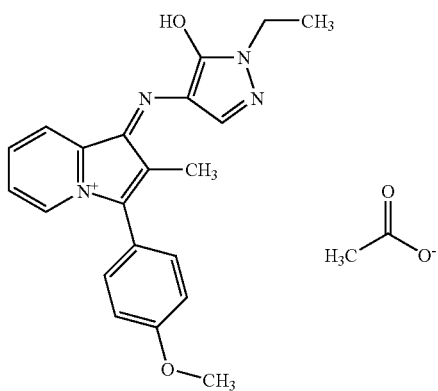

(1E)-1-[(1-ethyl-5-hydroxy-1H-pyrazol-4-yl)imino]-3-(4-methoxyphenyl)-2-methyl-1H-indolizinium-acetaet.

With 4-amino-antipyrine the following dye is obtained:

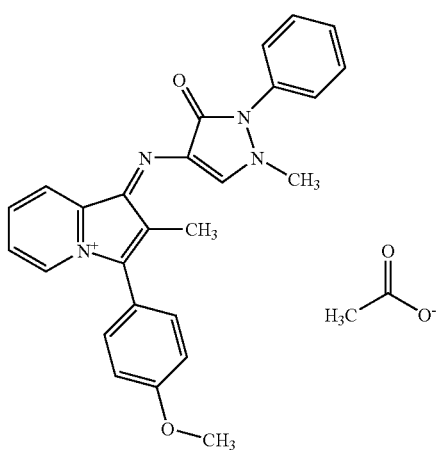

(1E)-3-(4-methoxyphenyl)-2-methyl-1-[(1-methyl-3-oxo-2-phenyl-2,3-dihydro-1H-pyrazol-4-yl)imino]-1H-indolizinium-acetate.

With 3-amino-4,5-dimethyl-2-hydroxy-1-phenylpyrrol the following dye is obtained:

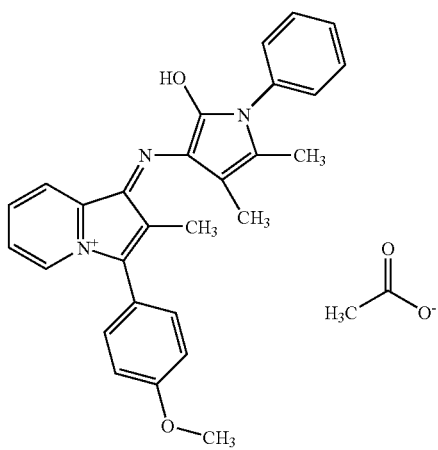

(1E)-1-[(2-hydroxy-4,5-dimethyl-1-phenyl-1H-pyrrol-3-yl)imino]-3-(4-methoxyphenyl)-2-methyl-1H-indolizinium-acetate.

With 4-amino-5-hydroxy-2-methyl-1-phenylimidazol the following dye is obtained:

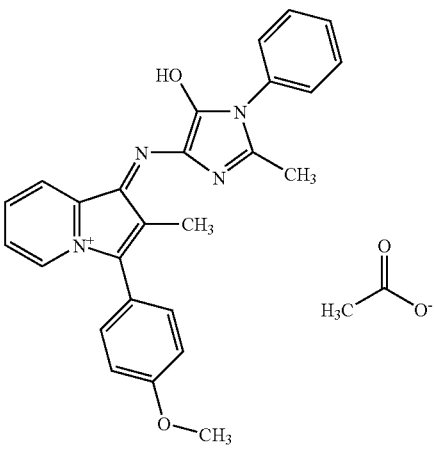

(1E)-1-[(5-hydroxy-2-methyl-1-phenyl-1H-imidazol-4-yl)imino]-3-(4-methoxyphenyl)-2-methyl-1H-indolizinium-acetate.

As a preferred ketone coupling partner for manufacturing the azacyanines, the following are particularly suitable: methylisatin, ethylisatin and $N^2$-hydroxy-ethyl-isatin.

With the use of methylisatin, the following dye is obtained:

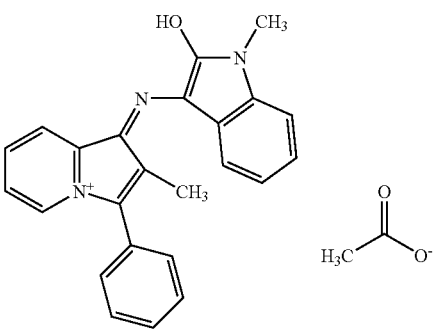

(1E)-1-[(2-hydroxy-1-methyl-1H-indol-3-yl)imino]-2-methyl-3-phenyl-1H-indolizinium-acetate, and, analogously, with ethylisatin, for example (1E)-1-[(2-hydroxy-1-ethyl-1H-indol-3-yl)imino]-2-methyl-3-phenyl-1H-indolizinium acatate, and, analogously, with $N^2$-hydroxyethyl-isatin, for example (1E)-1-{[2-hydroxy-1-(2-hydroxyethyl)-1H-indol-3-yl]imino}-2-methyl-3-phenyl-1H-indolizinium-acetate.

Additional preferred compounds having formula (I) are:

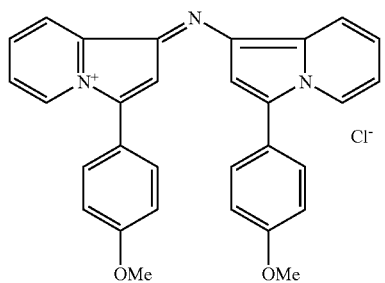

(1E)-3-(4-methoxyphenyl)-1-{[3-(4-methoxyphenyl)-1-indolizinyl]imino}-1H-indolizinium-chloride,

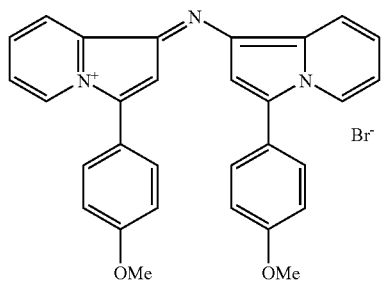

(1E)-3-(4-methoxyphenyl)-1-{[3-(4-methoxyphenyl)-1-indolizinyl]imino}-1-H-indolizinium-bromide,

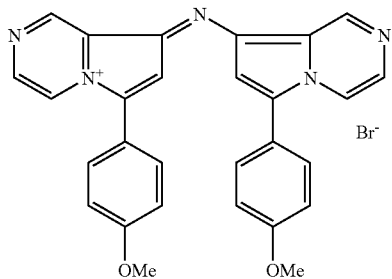

(8E)-6-(4-methoxyphenyl)-8-{[6-(4-methoxyphenyl)pyrrolo[1,2-a]pyrazin-8-yl]imino-}8H-pyrrolo[1,2-a]pyrazin-5-ium-bromide,

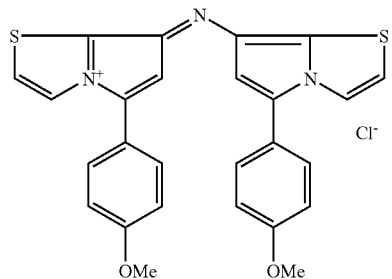

(7E)-5-(4-methoxyphenyl)-7-{[5-(4-methoxyphenyl)pyrrolo[2,1-b][1,3]thiazol-7-yl]imino}-7H-pyrrolo[2,1-b][1,3]thiazol-4-ium-chloride,

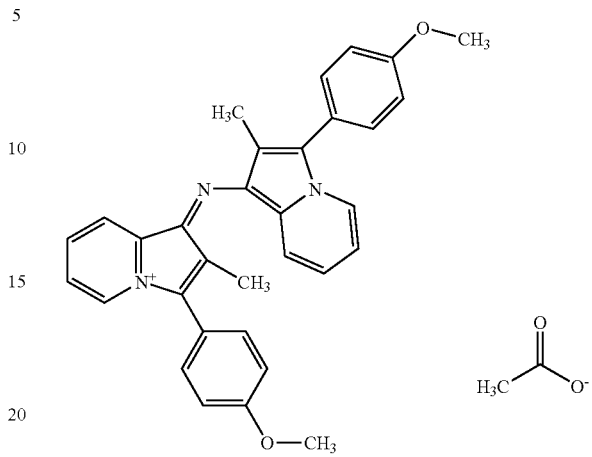

(1E)-3-(4-methoxyphenyl)-1-{[3-(4-methoxyphenyl)-2-methyl-1-indolizinyl]imino}-2-methyl-1H-indolizinium-acetate,

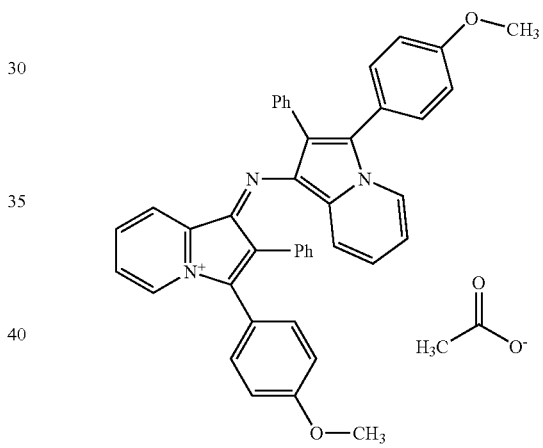

(1E)-3-(4-methoxyphenyl)-1-{[3-(4-methoxyphenyl)-2-phenyl-1-indolizinyl]imino}-2-phenyl-1H-indolizinium-acetate,

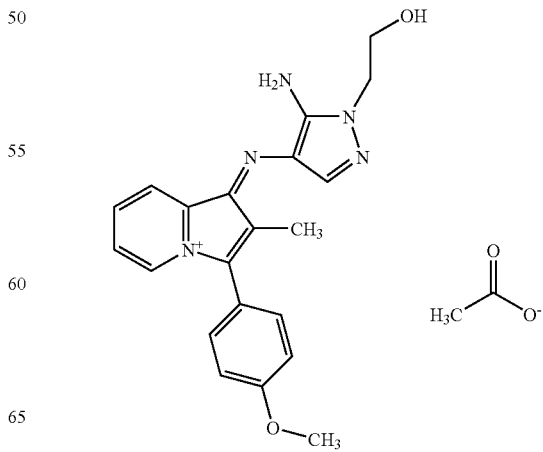

17

(1E)-1-{[5-amino-1-(2-hydroxyethyl)-1H-pyrazol-4-yl]imino}-3-(4-methoxyphenyl)-2-methyl-1H-indolizinium-acetate,

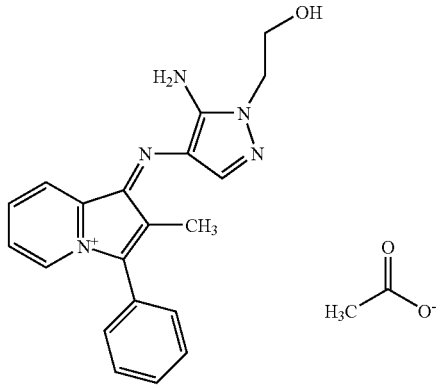

(1E)-1-{[5-amino-1-(2-hydroxyethyl)-1H-pyrazol-4-yl]imino}-2-methyl-3-phenyl-1H-indolizinium-acetate,

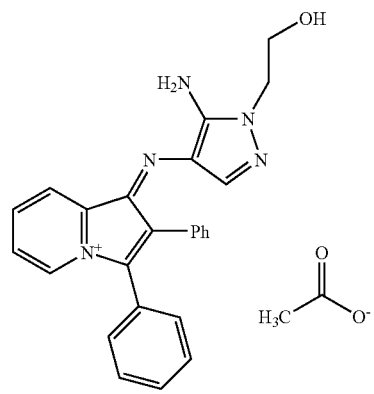

(1E)-1-{[5-amino-1-(2-hydroxyethyl)-1H-pyrazol-4-yl]imino}-2,3-diphenyl-1H-indolizinium-acetate,

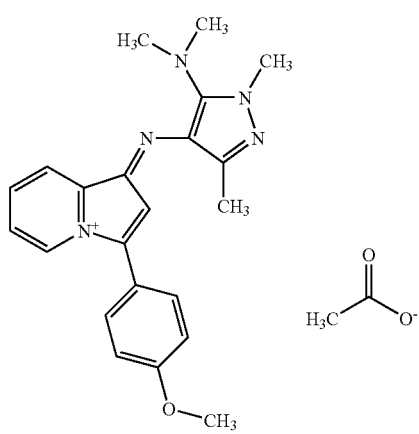

18

(1E)-1-{[5-(dimethylamino)-1,3-dimethyl-1H-pyrazol-4-yl]imino}-3-(4-methoxyphenyl)-1H-indolizinium-acetate,

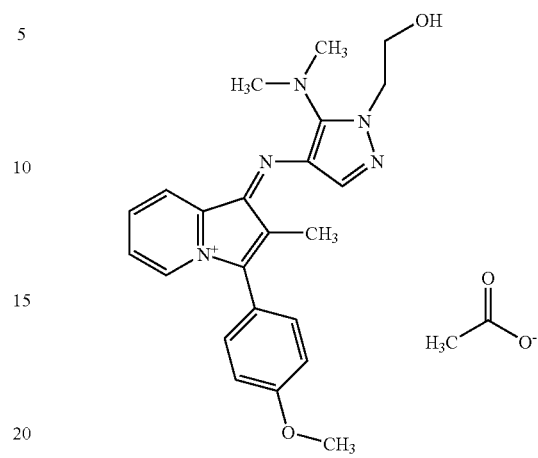

(1E)-1-{[5-(dimethylamino)-1-(2-hydroxyethyl)-1H-pyrazol-4-yl]imino}-3-(4-methoxyphenyl)-2-methyl-1H-indolizinium-acetate,

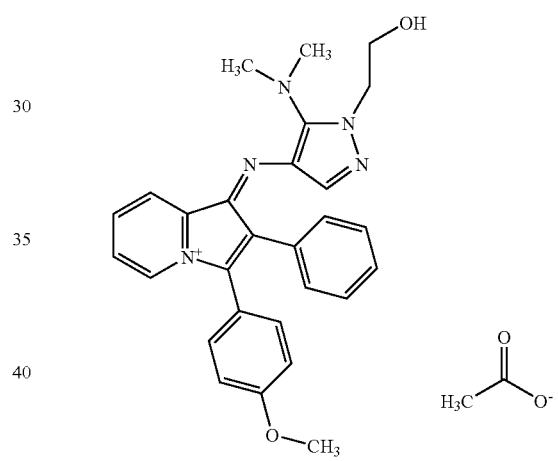

(1E)-1-{[5-(dimethylamino)-1-(2-hydroxyethyl)-1H-pyrazol-4-yl]imino}-3-(4-methoxyphenyl)-2-phenyl-1H-indolizinium-acetate,

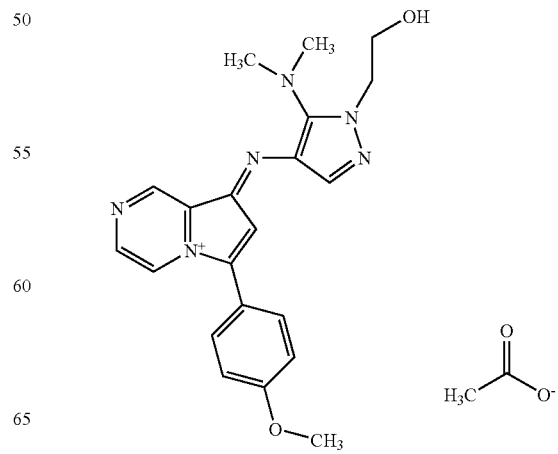

(8E)-8-{[5-(dimethylamino)-1-(2-hydroxyethyl)-1H-pyrazol-4-yl]imino}-6-(4-methoxyphenyl)-8H-pyrrolo[1,2-a]pyrazin-5-ium-acetate,

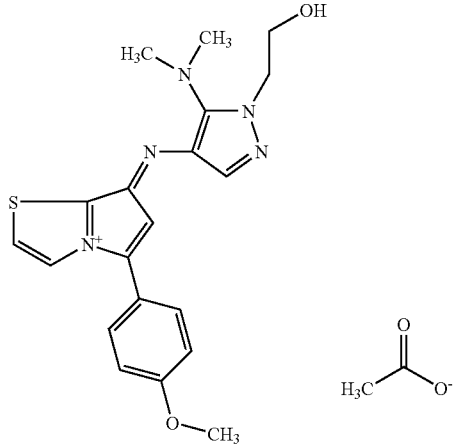

(7E)-7-{[5-(dimethylamino)-1-(2-hydroxyethyl)-1H-pyrazol-4-yl]imino}-5-(4-methoxyphenyl)-7H-pyrrolo[2,1-b][1,3]thiazol-4-ium-acetate,

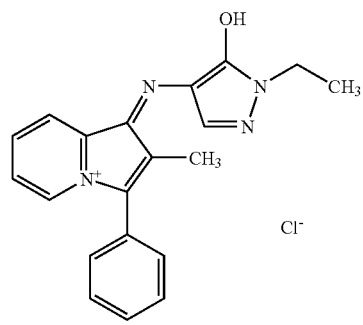

(1E)-1-[(1-ethyl-5-hydroxy-1H-pyrazol-4-yl)imino]-2-methyl-3-phenyl-1H-indolizini chloride,

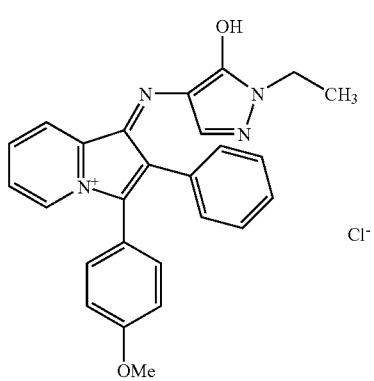

(1E)-1-[(1-ethyl-5-hydroxy-1H-pyrazol-4-yl)imino]-3-(4-methoxyphenyl)-2-phenyl-1H-indolizinium-chloride,

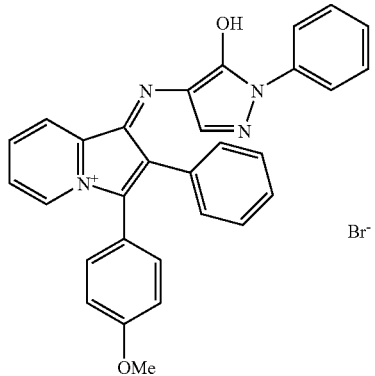

(1E)-1-[(5-hydroxy-1-phenyl-1H-pyrazol-4-yl)imino]-3-(4-methoxyphenyl)-2-phenyl-1H-indolizinium-bromide,

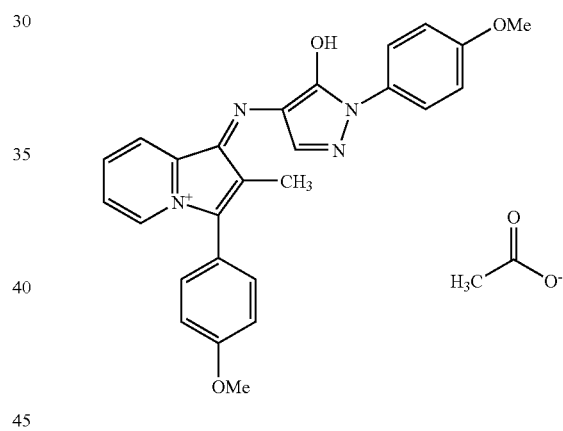

(1E)-1-{[5-hydroxy-1-(4-methoxyphenyl)-1H-pyrazol-4-yl]imino}-3-(4-methoxyphenyl)-2-methyl-1H-indolizinium-acetate,

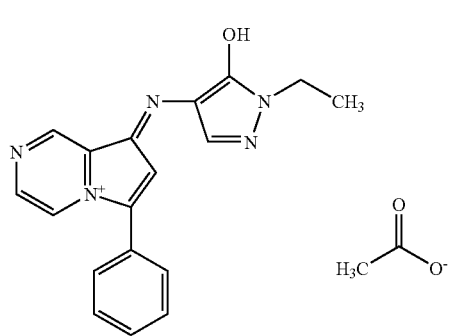

(8E)-8-[(1-ethyl-5-hydroxy-1H-pyrazol-4-yl)imino]-6-phenyl-8H-pyrrolo[1,2-a]p -ium-acetate,

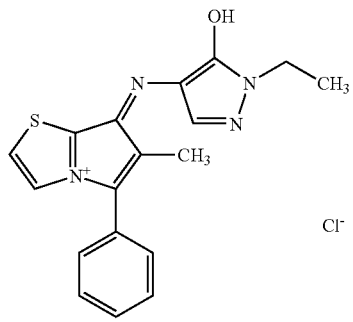

(7E)-7-[(1-ethyl-5-hydroxy-1H-pyrazol-4-yl)imino]-6-methyl-5-phenyl-7H-pyrrolo[2,1b][1,3]thiazol-4-ium-chloride,

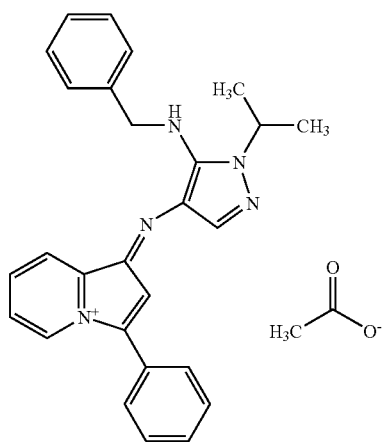

(1E)-1-{[5-(benzylamino)-1-isopropyl-1H-pyrazol-4-yl]imino}-3-phenyl-1H-indolizinium-acetate,

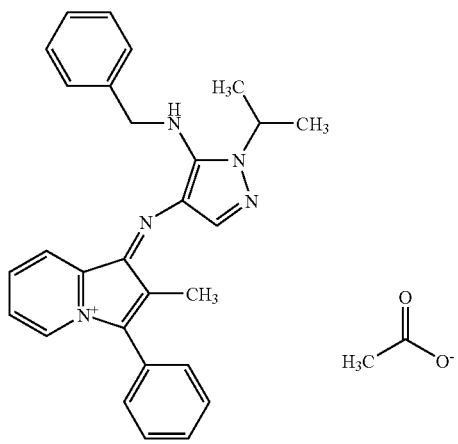

(1E)-1-{[5-(benzylamino)-1-isopropyl-1H-pyrazol-4-yl]imino}-2-methyl-3-phenyl-1H-indolizinium-acetate,

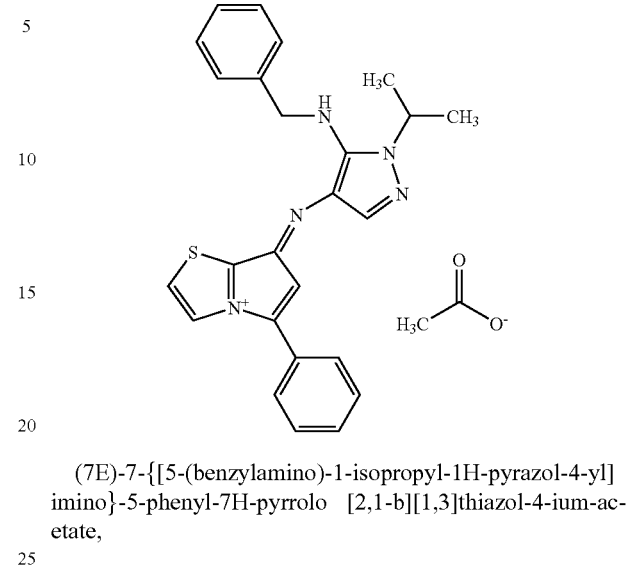

(7E)-7-{[5-(benzylamino)-1-isopropyl-1H-pyrazol-4-yl]imino}-5-phenyl-7H-pyrrolo [2,1-b][1,3]thiazol-4-ium-acetate,

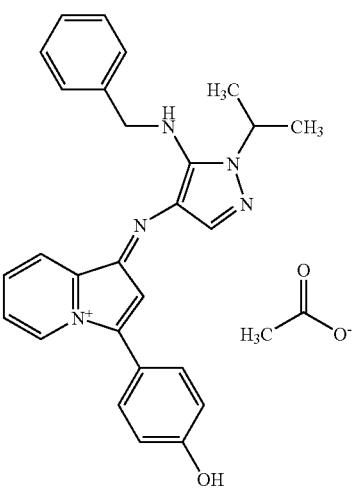

(1E)-1-{[5-(benzylamino)-1-isopropyl-1H-pyrazol-4-yl]imino}-3-(4-hydroxyphenyl)-1H-indolizinium-acetate,

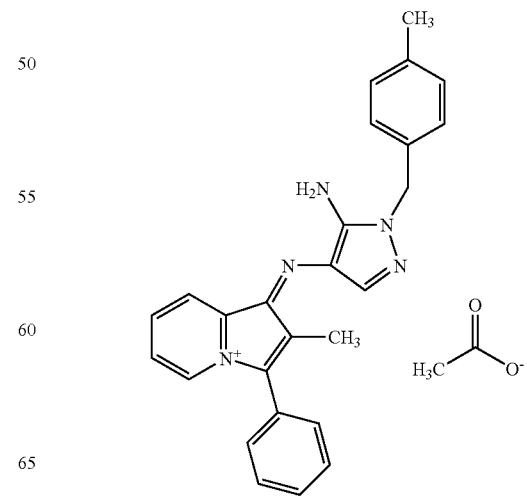

(1E)-1-{[5-amino-1-(4-methylbenzyl)-1H-pyrazol-4-yl]imino}-2-methyl-3-phenyl-1H-indolizinium-acetate, (1E)-1-[(1-ethyl-5-hydroxy-1H-pyrazol-4-yl)imino]-3-[4-(methyloxy)-phenyl]-1H-indolizinium-acetate,

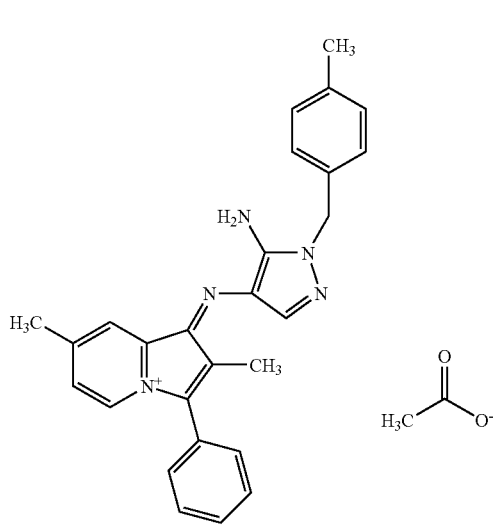

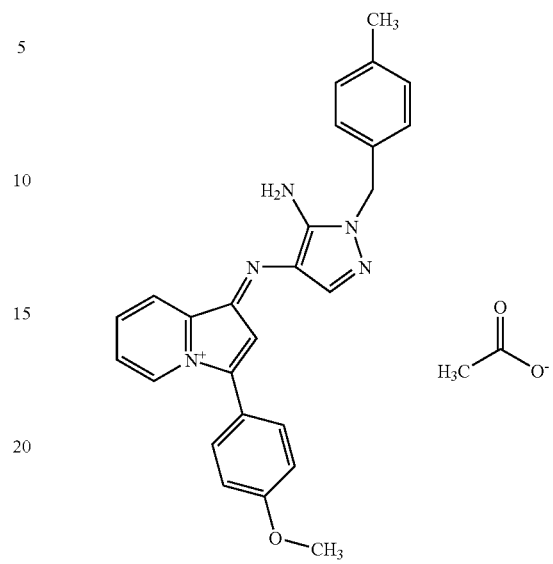

(1E)-1-{[5-amino-1-(4-methylbenzyl)-1H-pyrazol-4-yl]imino}-2,7-dimethyl-3-phenyl-1H-indolizinium-acetate, (1E)-1-({5-amino-1-[(4-methylphenyl)methyl]-1H-pyrazol-4-yl}imino)-3-[4-(methyloxy)phenyl]-1H-indolizinium-acetate,

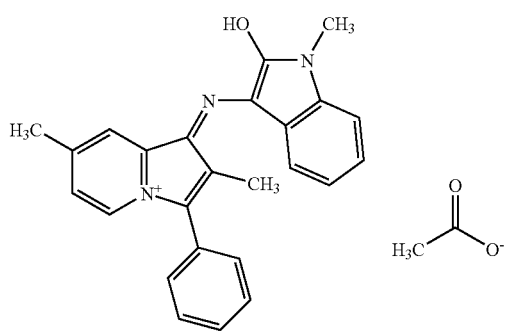

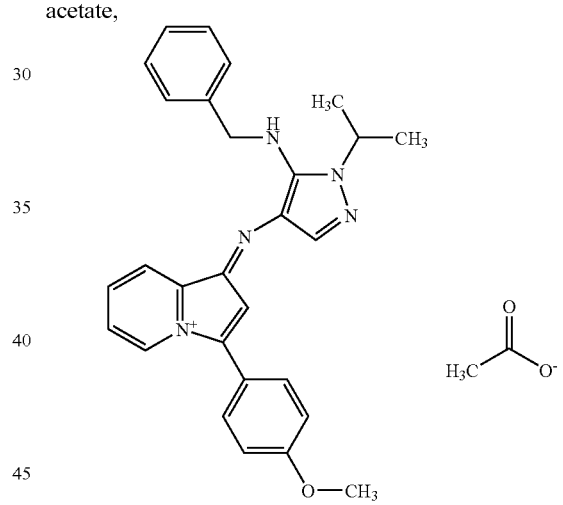

(1E)-1-[(2-hydroxy-1-methyl-1H-indol-3-yl)imino]-2,7-dimethyl-3-phenyl-1H-indolizinium-acetate, (1E)-1-({1-(1-methylethyl)-5-[(phenylmethyl)amino]-1H-pyrazol-4-yl}imino)-3-[4-(methyloxy)phenyl]-1H-indolizinium-acetate,

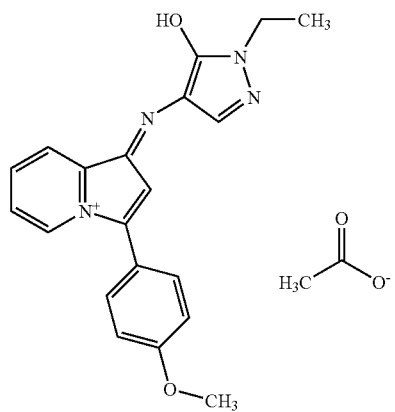

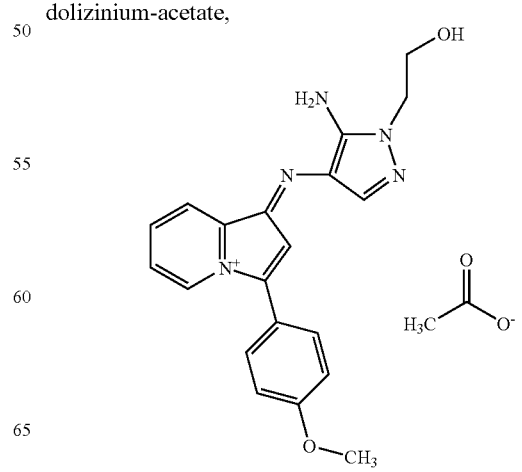

(1E)-1-{[5-amino-1-(2-hydroxyethyl)-1H-pyrazol-4-yl]imino}-3-[4-(methyloxy)phenyl[-1H-indolizinium-acetate,

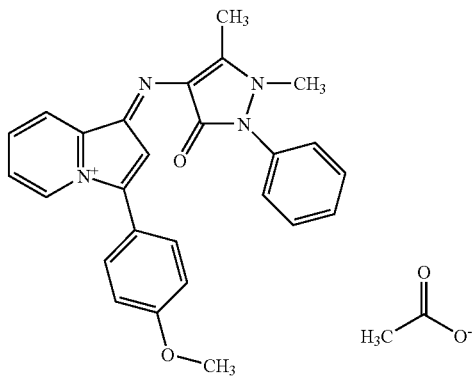

(1E)-1-[(1,5-dimethyl-3-oxo-2-phenyl-2,3-dihydro-1H-pyrazol-4-yl)imino]-3-[4-(methyloxy)phenyl]-1H-indolizinium-acetate,

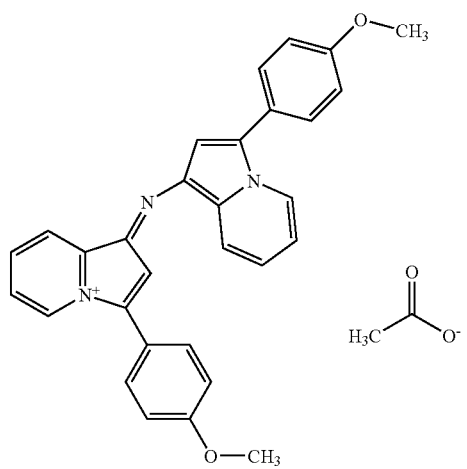

(1E)-3-[4-(methyloxy)phenyl]-1-({3-[4-(methyloxy)phenyl]-1-indolizinyl}imino)-1H-indolizinium-acetate,

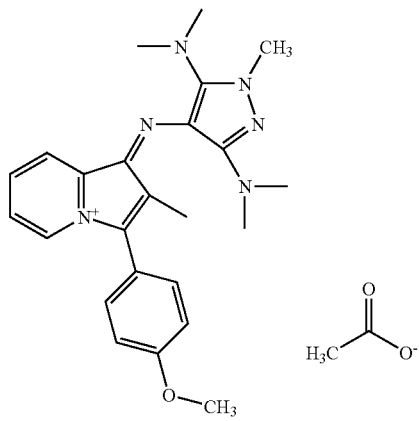

(1E)-1-{[3,5-bis(dimethylamino)-1-methyl-1H-pyrazol-4-yl]imino}-3-(4-methoxyphenyl)-2-methyl-1H-indolizinium-acetate The dyes having formula (I) are contained in the coloring agent in a total quantity of about 0.012 wt. % to about 15 wt. %, preferably about 0.05 wt. % to about 10 wt %.

In order to expand the color palette, besides the dyes having general formula (I), the coloring agent according to the present invention can contain additional natural or synthetic non-oxidative dyes.

Natural dyes include vegetable dyes such as henna or indigo while synthetic non-oxidative dyes azo dyes include triphenylmethane dyes, quinone dyes, and in particular nitro dyes, such as 1,4-bis[(2-hydroxyethyl)-amino]-2-nitrobenzene, 1-(2-hydroxyethyl)amino-2-nitro-4-[di(2-hydroxyethyl)-amino]-benzene, (HC Blue No. 2), 1-amino-3-methyl-4-[(2-hydroxyethyl) -amino]-6-nitrobenzene, (HC Violet No. 1), 4-[ethyl-(2-hydroxyethyl)amino]-1-[(2-hydroxyethyl)amino]-2-nitrobenzene-hydrochloride (HC Blue No. 12), 4-[di(2-hydroxyethyl)amino]-1-[(2-methoxyethyl) amino]-2-nitrobenzene, (HC Blue No. 11), 1-[(2,3-dihydroxypropyl)amino]-4-[methyl-(2-hydroxy-ethyl)amino]-2-nitrobenzene (HC Blue No. 10), 1-[(2,3-dihydroxy-propyl)-amino]-4-[ethyl-(2-hydroxyethyl)amino]-2-nitrobenzene-hydrochloride (HC Blue no. 9), 1-(3-hydroxypropylamino)-4-[di(2-hydroxyethyl)amino]-2-nitrobenzene, (HC Violet No. 2), 1-methylamino-4-[methyl-(2,3-dihydroxy-propyl) amino]-2-nitrobenzene (HC Blue No. 6), 2-((4-amino-2-nitrophenyl)-amino)-5-dimethyl-amino-benzoic acid (HC Blue No. 13), 1-(2-aminoethyl-amino)-4-[di(2-hydroxyethyl)amino]-2-nitrobenzene, 4-(di(2-hydroxyethyl)-amino)-2-nitro-1-phenylamino-benzene, 1-amino-4-[(2-hydroxyethyl)amino]-2-nitrobenzene (HC Red No. 7), 2-amino-4,6-dinitro-phenol, 1,4-diamino-2-nitrobenzene (CI76070), 4-amino-2-nitro-diphenylamine (HC Red No. 1), 1-amino-4-[di(2-hydroxyethyl)amino]-2-nitrobenzene-hydrochloride (HC Red No. 13), 1-amino-5-chlor-4-[(2-hydroxyethyl)amino]-2-nitrobenzene, 4-amino-1-[(2-hydroxyethyl)amino]-2-nitrobenzene (HC Red No. 3), 4-((2-hydroxyethyl)-methylamino)-1-(methylamino)-2-nitrobenzene, 1-amino-4-((2,3-dihydroxy-propyl)amino)-5-methyl-2-nitrobenzene, 1-amino-4-(methylamino)-2-nitrobenzene, 4-amino-2-nitro-1-((prop-2-ene-1-yl)amino)-benzene, 4-amino-3-nitrophenol, 4-[(2-hydroxyethyl) amino]-3-nitrophenol, 4-[(2-nitrophenyl)-amino]phenol (HC Orange No. 1), 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene, (HC Orange No. 3), 1-amino-5-chlor-4-[(2,3-dihydroxypropyl)amino]-2-nitrobenzene (HC Red No. 10), 5-chlor-1,4-[di(2,3-dihydroxypropyl)amino]-2-nitrobenzene (HC Red No. 11), 2-[(2-hydroxyethyl)amino]-4,6-dinitro-phenol, 4-ethylamino-3-nitrobenzoic acid, 2-[(4-amino-2-nitrophenyl)amino]-benzoic acid, 2-chlor-6-ethylamino-4-nitrophenol, 2-amino-6-chlor-4-nitrophenol, 4-[(3-hydroxy-propyl) amino]-3-nitrophenol, 2,5-diamino-6-nitropyridine, 6-amino-3-((2-hydroxyethyl)amino)-2-nitropyridin, 3-amino-6-((2-hydroxyethyl)amino)-2-nitropyridine, 3-amino-6-(ethylamino)-2-nitropyridine, 3-((2-hydroxyethyl)-amino)-6-(methylamino)-2-nitropyridine, 3-amino-6-(methylamino)-2-nitropyridine, 6-(ethylamino)-3-((2-hydroxyethyl)amino)-2-nitropyridine, 1,2,3,4-tetrahydro-6-nitroquinoxaline, 7-amino-3,4-dihydro-6-nitro-2H-1,4-benzoxazine (HC Red No. 14). 1,2-diamino-4-nitrobenzene (CI76020), 1-amino-2-[(2-hydroxyethyl)amino]-5-nitrobenzene (HC Yellow No. 5), 1-(2- hydroxyethoxy)-2-[(2-hydroxyethyl)amino]-5-nitrobenzene, (HC Yellow No. 4), 1-[(2-hydroxyethyl)amino]-2-nitrobenzene (HC Yellow No. 2), 2-(di(2-hydroxyethyl)amino)-5-nitrophenol, 2-[(2-hydroxyethyl)amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene-hydrochloride, (HC Yellow No. 9), 1-[(2-Ureidoethyl)amino]-4-nitrobenzene, 4-[(2,3-dihydroxypropyl)amino]-3-nitro-1-trifluormethyl-benzene, (HC Yellow No. 6), 1-chlor-2,4-bis[(2-hydroxyethyl)amino]-5-nitrobenzene (HC Yellow No. 10), 1-amino-4-((2-aminoethyl)amino)-5-methyl-2-nitrobenzene, 4-[(2-hydroxyethyl)amino]-3-nitro-1-methylbenzene, 1-chlor-4-[(2-hydroxyethyl)amino]-3-nitrobenzene (HC Yellow No. 12), 4-[(2-hydroxyethyl)amino]-3-nitro-1-trifluormethyl-benzene, (HC Yellow No. 13), 4-[(2-hydroxyethyl)amino]-3-nitro-benzonitril (HC Yellow No. 14), 4-[(2-hydroxyethyl)amino]-3-nitro-benzamid (HC Yellow No. 15), 3-((2-hydroxyethyl)amino)-4-methyl-1-nitrobenzene, 4-chlor-3-((2-hydroxyethyl)amino)-1-nitrobenzene, 2,4-dinitro-1-hydroxy-naphthalene, 1,4-di[(2,3-dihydroxypropyl)amino]-9,10-anthraquinone, 1,4-di[(2-hydroxyethyl)amino]-9,10-anthraquinone (CI61545, Disperse Blue 23), 1-[(2-hydroxyethyl)amino]-4-methylamino-9,10-anthraquinone (CI61505, Disperse Blue No. 3), 2-[(2-aminoethyl)amino]-9,10-anthraquinone (HC Orange No. 5), 1-amino-4-hydroxy-9,10-anthraquinone (CI60710, Disperse Red 15), 1-hydroxy-4-[(4-methyl-2-sulfophenyl)amino]-9,10-anthraquinone, 7-Beta-D-glucopyranosyl-9,10-dihydro-1-methyl-9,10-dioxo-3,5,6,8-tetrahydroxy-2-anthracenecarboxylic acid (CI75470, Natural Red 4), 1-[(3-aminopropyl)amino]-4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (CI62015, Disperse Red No. 11, Solvent Violet No. 26), 1,4-dihydroxy-5,8-bis[(2-hydroxyethyl)amino]-9,10-anthraquinone (CI62500, Disperse Blue No. 7, Solvent Blue No. 69), 1,4-diamino-9,10-anthraquinone (CI61100, Disperse Violet No. 1), 1-amino-4-(methylamino)-9,10-anthraquinone (CI61105, Disperse Violet No. 4, Solvent Violet No. 12), 2-hydroxy-3-methoxy-1,4-naphthoquinone, 2,5-dihydroxy-1,4-naphthoquinone, 2-hydroxy-3-methyl-1,4-naphthoquinone, N-(6-((3-chlor-4-(methylamino)phenyl)imino)-4-methyl-3-oxo-1,4-cyclohexadiene-1-yl)urea (HC Red No. 9), 2-((4-(di(2-hydroxyethyl)-amino)phenyl)amino)-5-((2-hydroxyethyl)amino)-2,5-cyclohexadiene-1,4-dione (HC Green No. 1), 5-hydroxy-1,4-naphthoquinone (CI75500, Natural Brown No. 7), 2-hydroxy-1,4-naphthoquinone (CI75480, Natural Orange No. 6), 1,2-dihydro-2-(1,3-dihydro-3-oxo-2H-indol-2-ylidene)-3H-indol-3-one (CI7300), 1,3-bis(dicyanomethylene)indane, 1-[di(2-hydroxyethyl)amino]-3-methyl-4-[(4-nitrophenyl)azo]-benzene (CI11210, Disperse Red No. 17), 1-[di(2-hydroxyethyl)amino]-4-[(4-nitrophenyl)azo]-benzene (Disperse Black No. 9), 4-[(4-aminophenyl)azo]-1-[di(2-hydroxyethyl)amino]-3-methylbenzene, (HC Yellow No. 7), 2,6-diamino-3-[(pyridin-3-yl)azo]-pyridine, 2-((4-(acetylamino)phenyl)azo)-4-methylphenol (CI11855; Disperse Yellow No. 3) or 2-((4-(Ethyl(2-hydroxyethyl)amino)-2-methylphenyl)azo)-5-nitro-1,3-thiazol (CI111935; Disperse Blue No. 106).

Furthermore, additional basic (=cationic) dyes can also be included, such as 9-(dimethylamino)-benzo[a]-phenoxazin-7-ium-chloride (CI51175; Basic Blue No. 6), di[4-(diethylamino)-phenyl][4-(ethylamino)naphthyl]carbenium-chloride (CI42595; Basic Blue No. 7), di-(4-(dimethylamino)phenyl)-(4-(methyl-phenylamino)naphthalene-1-yl) carbenium-chloride (CI42563; Basic Blue No. 8), 3,7-di(dimethylamino)-phenothiazin-5-ium-chloride (CI52015; Basic Blue No. 9), di[4-(dimethylamino)phenyl][4-(phenylamino)naphthyl]carbenium-chloride (CI44045; Basic Blue No. 26), 2-[(4-(ethyl(2-hydroxyethyl)amino)-phenyl)azo]-6-methoxy-3-methyl-benzothiazolium-methylsulfate (CI11154; Basic Blue No. 41), Basic Blue No. 77, 8-amino-2-brom-5-hydroxy-4-imino-6-[(3-(trimethylammonio)phenyl)-amino]-(4H)-naphthalenone-chloride (CI56059; Basic Blue No. 99), bis[4-(dimethylamino)phenyl][4-(methylamino)phenyl]carbenium-chloride (CI42535; Basic Violet No. 1), tri(4-amino-3-methylphenyl)carbenium-chloride (CI42520; Basic Violet No. 2), tris[4-(dimethylamino)phenyl]-carbenium-chloride (CI42555; Basic Violet No. 3), 2-[3,6-(diethylamino)-dibenzopyranium-9-yl]-benzoic acid-chloride (CI45170; Basic Violet No. 10), di(4-aminophenyl)(4-amino-3-methylphenyl)carbenium-chloride (CI42510; Basic Violet No. 14), 1,3-bis[(2,4-diamino-5-methylphenyl)azo]-3-methylbenzene (CI21010; Basic Brown No. 4), 1-[(4-aminophenyl)azo]-7-(trimethylammonio)-2-naphthol-chloride (CI12250; Basic Brown No. 16), 3-[(4-amino-2,5-dimethoxyphenyl)-azo]-N,N,N-trimethylbenzolaminium-chloride (CI112605, Basic Orange No. 69), 1-[(4-amino-2-nitrophenyl)azo]-7-(trimethylammonio)-2-naphthol-chloride (Basic Brown No. 17), 1-[(4-amino-3-nitrophenyl)azo]-7-(trimethylammonio)-2-naphthol-chloride (CI12251; Basic Brown No. 17), 2-((4-aminophenyl)azo)-1,3-dimethyl-1H-imidazol-3-ium-chloride (Basic Orange No. 31), 3,7-diamino-2,8-dimethyl-5-phenylphenazinium-chloride (CI50240; Basic Red No. 2), 1,4-dimethyl-5-[(4-(dimethylamino)phenyl)azo]-1,2,4-triazolium-chloride (CI11055; Basic Red No. 22), 1,3-dimethyl-2-((4-dimethylamino)phenyl)azo-1H-imidazol-3-ium-chloride (Basic Red No. 51), 2-hydroxy-1-[(2-methoxyphenyl)azo]-7-(trimethylammonio)-naphthalene-chloride (CI12245; Basic Red No. 76), 2-[2-((2,4-dimethoxyphenyl)amino)ethenyl]-1,3,3-trimethyl-3H-indol-1-ium-chloride (CI48055; Basic Yellow No. 11), 3-methyl-1-phenyl-4-[(3-(trimethylammonio)phenyl)azo]-pyrazol-5-on-chloride (CI12719; Basic Yellow No. 57), di[4-(dimethylamino)phenyl]iminomethan-hydrochloride (CI41000; Basic Yellow No. 2), 1-methyl-4-((methylphenylhydrazono)-methyl)-pyridinium-methylsulfate (Basic Yellow No. 87), bis[4-(diethylamino)-phenyl]phenylcarbenium-bisulfate(1:1) (CI42040; Basic Green No. 1), di(4-(dimethylamino)phenyl)-phenylmethanol (CI42000; Basic Green No. 4), 1-(2-morpholiniumpropylamino)-4-hydroxy-9,10-anthraquinone-methylsulfate, 1-[(3-(dimethyl-propylaminium)propyl)-amino]-4-(methylamino)-9,10-anthraquinone-chloride, 1,4-dimethyl-5-[(4-(dimethylamino)phenyl)azo]-1,2,4-triazolium-chloride (C.I. 11055; Basic Red 22), 1-methyl-4-{[methyl-(phenyl)hydrazono]methyl}pyridinium-chloride (Basic Yellow 87), 1-methyl-4-{(E)-[methyl(4-methoxy-phenyl)hydrazono]-methyl}pyridinium-chloride, 1-methyl-4-({methyl[4-methoxy-phenyl]-hydrazono}methyl)pyridinium-methylsulfate (Basic Yellow 91), 2-{[4-(dimethylamino)phenyl]azo}-1,3-dimethyl-1H-imidazol-3-ium-chloride (Basic Red 51), 5-{[4-(dimethylamino)-phenyl]azo}-1,2-dimethyl-1H-pyrazol-2-ium-chloride, 1,3-dimethyl-2-{[4-(methylamino)phenyl]azo}-1H-imidazol-3-ium-chloride (Basic Red 109), 2-[(4-aminophenyl)azo]-1,3-dimethyl-1H-imidazol-3-ium-chloride, 4-{[4-(dimethylamino)phenyl]azo}-1-methylpyridinium-chloride or N,N-dimethyl-4-[(E)-(1-oxido-4-pyridinyl)-diazenyl]aniline.

Depending on the color vehicle used, in specific cases anionic ("acid") dyes that are compatible with the cationic dyes used can also be added, such as, for example, 6-hydroxy-5-[(4-sulfophenyl)azo]-2-naphthalene sulfonic acid-disodium salt (CI15985; Food Yellow No. 3; FD&C Yellow No. 6), 2,4-dinitro-1-naphthol-7-sulfonic acid-disodium salt (CI10316; Acid Yellow No. 1; Food Yellow No. 1), 2-(indan-1,3-dion-2-yl)quinolin-x,x-sulfonic acid (mixture of mono- and disulfonic acids) (CI47005; D&C Yellow No. 10; Food Yellow No. 13, Acid Yellow No. 3), 5-hydroxy-1-(4-sulfophenyl)-4-[(4-sulfophenyl)azo]pyrazol-3-carboxylic acid-trisodium salt (CI19140; Food Yellow No. 4; Acid Yellow No. 23), 9-(2-carboxyphenyl)-6-hydroxy-3H-xanthen-3-one (CI45350; Acid Yellow No. 73; D&C Yellow No. 8), 4-((4-amino-3-sulfophenyl)azo)-benzenesulfonic acid-disodium salt (CI13015, Acid Yellow No. 9), 5-[(2,4-dinitrophenyl)amino]-2-phenylamino-benzenesulfonic acid-sodium salt (CI10385; Acid Orange No. 3), 4-[(2,4-dihydroxyphenyl)azo]-benzenesulfonic acid-monosodium salt (CI14270; Acid Orange No. 6), 4-[(2-hydroxynaphth-1-yl)azo]-benzene sulfonic acid-sodium salt (CI15510; Acid Orange No. 7), 4-((2-hydroxy-naphthalene-1-yl)azo)-3-methyl-benzenesulfonic acid-sodium salt (CI15575; Acid Orange No. 8), 4-[(2,4-dihydroxy-3-[(2,4-dimethylphenyl)azo]phenyl)azo]-benzenesulfonic acid-sodium salt (CI20170; Acid Orange No. 24), 3',6'-dihydroxy-4',5'-diiodospiro(isobenzofuran-1(3H)-9'-(9H)xanthene)-3-one (CI45425, D&C Orange No. 10), 4-hydroxy-3-[(4-sulfonaphth-1-yl)azo]-1-naphthalene-sulfonic acid-disodium salt (CI14720; Acid Red No. 14), 4-hydroxy-3-[(2-methoxyphenyl)azo]-1-naphthalenesulfonic acid-monosodium salt (CI14710; Acid Red No. 4), 6-hydroxy-5-[(4-sulfonaphth-1-yl)azo]-2,4-naphthalene-disulfonic acid-trisodium salt (CI16255; Ponceau 4R; Acid Red No. 18), 3-hydroxy-4-[(4-sulfonaphth-1-yl)azo]-2,7-naphthalene-disulfonic acid-trisodium salt (CI16185; Acid Red No. 27), 8-amino-1-hydroxy-2-(phenylazo)-3,6-naphthalene-disulfonic acid-disodium salt (CI17200; Acid Red No. 33), 5-(Acetylamino)-4-hydroxy-3-[(2-methylphenyl)azo]-2,7-naphthalene-disulfonic acid-disodium salt (CI18065; Acid Red No. 35), 2-(3-hydroxy-2,4,5,7-tetraioddibenzopyran-6-on-9-yl)-benzoic acid-disodium salt (CI45430; Acid Red No. 51), N-[6-(diethylamino)-9-(2,4-disulfophenyl)-3H-xanthen-3-yliden]-N-ethylethanammonium-hydroxide, internal salt, sodium salt (CI45100; Acid Red No. 52), 8-[(4-(Phenylazo)phenyl)azo]-7-naphthol-1,3-disulfonic acid-disodium salt (CI27290; Acid Red No. 73), 2',4',5',7'-Tetrabrom-3',6'-dihydroxyspiro[-isobenzofuran-1 (3H), 9'-[9H]xanthen]-3-on-disodium salt (CI45380; Acid Red No. 87), 2',4',5',7'-Tetrabrom-4,5,6,7-tetrachlor-3',6'-dihydroxyspiro[isobenzofuran-1(3H), 9'[9H]xanthen]-3-on-disodium salt (CI45410; Acid Red No. 92), 3',6'-dihydroxy-4',5'-diiodospiro-[isobenzofuran-1(3H), 9'(9H)-xanthen]-3-on-disodium salt (CI45425; Acid Red No. 95), 2-hydroxy-3-((2-hydroxynaphth-1-yl)azo)-5-nitro-benzenesulfonic acid-monosodium salt (CI15685; Acid Red No. 184), (2-Sulfophenyl)di[4-(ethyl((4-sulfophenyl)methyl)amino)phenyl]-carbenium-disodium salt, betaine (CI42090; Acid Blue No. 9; FD&C Blue No. 1), 3-hydroxy-4-((4-methyl-2-sulfophenyl)azo)-2-naphthalenecarboxylic acid-disodium salt (CI15850; FD&C Red No. 6), 6-hydroxy-5-((2-methoxy-5-methyl-4-sulfophenyl)azo)-2-naphthalene-sulfonic acid-disodium salt (CI16035; FD&C Red 40), 1,4-Bis[(2-sulfo-4-methylphenyl)amino]-9,10-anthraquinone-disodium salt (CI61570; Acid Green No. 25), Bis[4-(dimethylamino)phenyl]-(3,7-disulfo-2-hydroxy-naphth-1-yl)carbenium-internal salt, monosodium salt (CI44090; Food Green No. 4; Acid Green No. 50), Bis[4-(diethylamino)phenyl](2,4-disulfophenyl)carbenium-internal salt, sodium salt (2:1) (CI42045; Food Blue No. 3; Acid Blue No. 1), Bis[4-(diethylamino)phenyl](5-hydroxy-2,4-disulfophenyl)carbenium-internal salt, calcium salt (2:1) (CI42051; Acid Blue No. 3), 1-amino-4-(cyclohexylamino)-9,10-anthraquinone-2-sulfonic acid-sodium salt (CI62045; Acid Blue No. 62), 3,3-bis(3,5-dibrom-4-hydroxyphenyl)-4,5,6, 7-tetrabrom-2,1(3h)-benzoxathiol-1,1-dioxide, 1-amino-4-(phenylamino)-9,10-anthraquinone-2-sulfonic acid (CI62055; Acid Blue No. 25), 2-(1,3-dihydro-3-oxo-5-sulfo-2H-indol-2-yliden)-2,3-dihydro-3-oxo-1H-indol-5-sulfonic acid-disodium salt (CI73015; Acid Blue No. 74), 9-(2-carboxyphenyl)-3-[(2-methylphenyl)amino]-6-[(2-methyl-4-sulfophenyl)amino]xanthylium-internal salt, monosodium salt (CI45190; Acid Violet No. 9), 1-hydroxy-4-[(4-methyl-2-sulfophenyl)amino]-9,10-anthraquinone-sodium salt (CI60730; D&C Violet No. 2; Acid Violet No. 43), Bis[3-nitro-4-[(4-phenylamino)-3-sulfo-phenylamino]-phenyl]-sulfone (CI10410; Acid Brown No. 13), 5-amino-4-hydroxy-6-[(4-nitrophenyl)azo]-3-(phenylazo)-2,7-naphthalene-disulfonic acid-disodium salt (CI20470; Acid Black No. 1), 3-hydroxy-4-[(2-hydroxynaphth-1-yl)azo]-7-nitro-1-naphthalene-sulfonic acid-chromium complex (3:2) (CI15711; Acid Black No. 52), 3-[(2,4-dimethyl-5-sulfophenyl)azo]-4-hydroxy-1-naphthalene-sulfonic acid-disodium salt (CI14700; Food Red No. 1; Ponceau SX; FD&C Red No. 4), 4-(Acetylamino)-5-hydroxy-6-[(7-sulfo-4-[(4-sulfophenyl)azo]naphth-1-yl)azo]-1,7-naphthalenedisulfonic acid-tetrasodium salt (CI28440; Food Black No. 1), 3-hydroxy-4-(3-methyl-5-oxo-1-phenyl-4,5-dihydro-1H-pyrazol-4-ylazo)-naphthalene-1-sulfonic acid-sodium salt, chromium complex (Acid Red No. 195).

The total content of additional natural and/or synthetic non-oxidative dyes in the coloring agent according to the present invention is about 0.01 wt. % to 15 wt %, in particular about 0.1 wt. % to about 12 wt %.

Of course, oxidative dye precursors, such as, for example, paraphenylendiamines, metaphenylendiamines, aminophenoles, or 4,5-diaminopyrazoles, can also be added to the coloring agent according to the present invention.

The additional developer substances and coupler substances can be contained in the coloring agent with a respective total quantity of about 0.01 wt. % to about 20 wt %, preferably about 0.1 wt. % to about 10 wt %, and in particular 0.1 wt. % to 5 wt %.

In order to increase the color intensity, the carriers standardly used in cosmetic systems can be added as necessary. Suitable compounds are described, for example, in German Patent No. DE-OS 196 18 595. Especially suitable carriers are, for example, benzyl alcohol, vanillin, and isovanillin.

For dyeing, the dyes described above are applied in a suitable color vehicle.

The formulation of the dye according to the present invention can be, for example, a solution, in particular an aqueous or aqueous-alcoholic solution. However, the especially preferred formulations are a cream, a gel, an emulsion, or a powdered or granulate formulation. Their composition is a mixture of the dyes with the additives that are usual for such formulations.

Standard additives in solutions, creams, emulsions, gels, powders or granulates include, for example, solvents such as water, lower aliphatic alcohols, e.g., ethanol, propanol, or isopropanol, glycerin or glycols such as 1,2-propyleneglycol, as well as wetting agents or emulsifying agents from the classes of the anionic, cationic, amphoteric or nonionic surface-active substances, such as, for example, fatty alcohol sulfates, oxyethylated fatty alcohol sulfates, alkylsulfonates, alkylbenzenesulfonates, alkyl trimethyl ammonium salts, alkylbetaines, oxyethylated fatty alcohols, oxyethylated nonylphenols, fatty acid alkanol-amides and oxyethylated fatty acid esters, as well as thickeners such as higher fatty alcohols, starches, cellulose derivates, petroleum jelly, paraffin oil, sugar and fatty acids, as well as conditioning agents such as cationic resins, cationic, nonionic, anionic and amphoteric polymers, lanolin derivates, cholesterine, pantothenic acid, and betaine. The mentioned components are used in standard quantities for such purposes; for example, the wetting agents and emulsifying agents are used in concentrations of about 0.1 wt. % to 30 wt %, the thickeners are used in a quantity of about 0.1 wt. % to about 30 wt %, and the conditioning agents are used in a concentration of about 0.1 wt. % to about 5.0 wt %.

In addition, the coloring agent can contain additional standard additives, for example, antioxidants such as ascorbic acid, mercaptoacetic acid or sodium sulfite, as well as perfume oils, penetrating agents, buffer systems, complex formers, preservatives, wetting agents, emulsifiers, thickeners, encapsulating agents, granulating agents, and conditioning agents.

The ready-to-use coloring agent according to the present invention can be applied full-strength or can be created immediately before use by mixing the color vehicle containing the dyes with water, a conditioning product, or an oxidizing agent.

The main oxidizing agents that can be used include hydrogen peroxide or its additive compounds with urea, melamine, sodium borate or sodium carbonate, in the form of a 1% to 12%, preferably a 3% to 6%, aqueous solution. For agents with simultaneous lightening or bleaching, depending on the formula (I) dye used, persulfates can also be added, e.g., ammonium persulfate, potassium persulfate, or sodium persulfate. The weight ratio between the color vehicle and the oxidizing agent is here preferably about 5:1 to 1:3, in particular 1:1 to 1:2. Larger quantities of oxidizing agents are used above all with higher concentrations of oxidative dye precursors in the coloring agent, or if a stronger bleaching of the keratin fibers (in particular the hair) is intended.

The pH value of the ready-to-use coloring agent according to the present invention can be set such that it can be applied full-strength, or during the mixing of the color vehicle with a thinning agent (conditioner, water, etc.) or the oxidizing agent a pH value arises that is determined by the pH values of the color vehicle and of the thinning agent, or of the oxidizing agent, as well as by the mixing ratio.

The ready-to-use agent has a pH value of 2 to 11, preferably 5 to 11. The setting of an alkaline pH value here preferably takes place using ammonia, but it is also possible for this purpose to use organic amines, such as 2-amino-2-methyl-1-propanol, tris(hydroxymethyl)aminomethane, monoethanolamine and triethanolamine, or mixtures of organic amines and ammonia, as well as inorganic bases such as sodium hydroxide and potassium hydroxide. If the pH values are too high, a correction can take place using inorganic or organic acids, e.g., phosphoric acid, acetic acid, lactic acid, ascorbic acid, citric acid, or tartaric acid.

Subsequently, a quantity sufficient for the color treatment, in general about 60 grams to about 200 grams, is applied to the keratin fibers in pure form or in the form of the mixture, and the dye preparation is allowed to act on the keratin fibers at about 15° C. to 50° C., preferably about 30° C. to about 40° C., for about 10 minutes to about 45 minutes, preferably about 30 minutes; the keratin fibers are then rinsed with water and dried. If necessary, after this rinsing washing takes place with a shampoo, and subsequent rinsing may take place with a weak organic acid, such as citric acid or tartaric acid. Subsequently, the keratin fibers are dried.

The coloring agent with cationic azacyanine dyes having formula (I) enables, among other things, a simple and gentle dyeing of hairs having differing degrees of damage (for example, recoloring of already oxidatively dyed sections of hair), the color vehicle being applied to the previously damaged hair sections (e.g., the hair tips) without oxidizing agents—in pure form or mixed with an acidic, neutral, or basic aqueous thinning agent—while the color vehicle mixed with the oxidizing agent is applied to the hair sections that are previously damaged only slightly or not at all (for example, newly grown hair). The aqueous components used for the thinning can contain the above-cited standard additives for solutions, creams, emulsions, or gels. This method enables dyeing processes that are adapted to the condition of the hair, distinguished by a protective balance between the roots and the hair tips, which is not possible with the use of standard oxidative hair coloring agents, because an oxidizing agent is always required for the coupling of the dye precursors.

The coloring agent according to the present invention is distinguished by dyeings having especially high color intensity and brilliance, a good color balance between damaged and undamaged hair (for example, between hair tips and newly grown hair), good durability, very good hair protection, and variable possibilities of use, with and without oxidizing agents.

A further subject matter of the present application is new asymmetrical cationic azacyanine dyes having formula (I), "asymmetrical" meaning those compounds of formula (I) in which the residue B situated at nitrogen is different from the ring system also situated at this nitrogen.

The following examples are intended to explain the subject matter of the present invention in more detail, without limiting it to these examples.

EXAMPLES

Example 1

Synthesis of (1E)-1-[(1-ethyl-5-hydroxy-1H-pyrazol-4-yl)imino]-3-[4-(methyloxy)phenyl]-1H-indolizinium-acetate Stage 1: Synthesis of 2-[3-(4-methoxyphenyl)-1-oxoprop-2-enyl]pyridine 7.4 g 2-acetylpyridine is added to a solution of 8.3 g 4-methoxybenzaldehyde in 100 ml methanol at 0° C. 100 ml of a 2 N sodium hydroxide solution is added with strong agitation. After 14 hours of agitation at room temperature, the yellow precipitate is filtered off, washed with 10 ml methanol and washed three times with 50 ml water, and dried in a vacuum.

Yield: 11.4 g (78% of theory).

Stage 2: Synthesis of (1E)-1-[(1-ethyl-5-hydroxy-1H-pyrazol-4-yl)imino]-3-[4-(methyloxy)phenyl]-1H-indolizinium-acetate 0.12 g 2-[3-(4-methoxyphenyl)-1-oxoprop-2-enyl]pyridine and 0.11 g 4-amino-1-ethyl-hydroxy-1H-pyrazol-sulfate (1:1) are agitated in 3 ml glacial acetic acid for 1 hour at room temperature and then agitated for 2 hours at 50° C. Water (20 ml) is added, setting the pH value to about 5.

Subsequently, the violet precipitate is filtered, washed with 2×5 ml water, and dried in a vacuum.

Yield: 0.12 g (60% of theory).

ESI-MS: 347 [M+] (81)

Example 2

Hair Coloring Agent

| | |
|---|---|
| (1E)-1-[(1-ethyl-5-hydroxy-1H-pyrazol-4-yl)imino]-3-[4-(methyloxy)-phenyl]-1H-indolizinium-acetate (dye having formula (VI) with R1' = 4-methoxyphenyl, R3' = hydrogen and Y = acetate) | 1.0 g |
| Ethanol | 30.0 g |
| Laureth-4 | 0.5 g |
| Water, completely desalinated | balance to 100.0 g |

The pH value is set to 10 with 25% ammonia.

5 g of the above color vehicle is mixed with 5 g of a 6% hydrogen peroxide solution. The obtained ready-to-use hair coloring agent is applied to bleached hair locks and is uniformly distributed using a brush. After an action period of 20 minutes at 40° C., the hair is rinsed with lukewarm water and is washed with shampoo, rinsed with lukewarm water, and then dried.

An intensively blue-violet colored lock is obtained.

Example 3

Hair Coloring Agent

| | |
|---|---|
| (1E)-3-[4-(Methyloxy)phenyl]-1-({3-[4-(methyloxy)phenyl]-1-indolizinyl}imino)-1H-indolizinium-acetate (dye having formula (II) with R2' = R2 = H, R3' = R3 = H, X' = X = 4-Methoxy; Y = acetate) | 1.0 g |
| Ethanol | 40.0 g |
| Laureth-4 | 0.5 g |
| Water, completely desalinated | balance to 100.0 g |

The pH value is set to 10 with 25% ammonia.

5 g of the above color vehicle is mixed with 5 g of a 6% hydrogen peroxide emulsion. The obtained ready-to-use hair coloring agent is applied to bleached hair locks and distributed uniformly using a brush. After an action period of 20 minutes at 40° C., the hair is rinsed with lukewarm water, washed with shampoo, rinsed with lukewarm water, and then dried.

A deep blue dyed lock is obtained.

Example 4

Hair Coloring Agent

| | |
|---|---|
| (1E)-1-({5-amino-1-[(4-methylphenyl)methyl]-1H-pyrazol-4-yl}imino)-3-[4-(methyloxy)phenyl]-1H-indolizinium-acetate (Dye having formula (IV) with R1' = 4-methoxyphenyl, R3' = hydrogen, Y = acetate) | 0.5 g |
| Ethanol | 30.0 g |
| Cetyltrimethylammonium chloride | 0.5 g |
| Water, completely desalinated | balance to 100.0 g |

The pH value is set to 10 with 25% ammonia.

5 g of the above color vehicle is applied to bleached hair locks and distributed uniformly using a brush. After an action period of 20 minutes at 40° C., the hair is rinsed with lukewarm water, washed with a shampoo, rinsed again with lukewarm water, and then dried.

A deep red-violet dyed lock is obtained.

Example 5

Hair Coloring Agent

| | |
|---|---|
| (1E)-1-({1-(1-methylethyl)-5-[(phenylmethyl)amino]-1H-pyrazol-4-yl}imino)-3-[4-(methyloxy)phenyl]-1H-indolizinium-acetate (dye having formula (V) with R1' = 4-methoxyphenyl, R3' = hydrogen, Y = acetate) | 1.0 g |
| Ethanol | 30.0 g |
| Laureth-4 | 0.5 g |
| Water, completely desalinated | balance to 100.0 g |

The pH value is set to 10 with 25% ammonia.

5 g of the above color vehicle is mixed with 5 g of a 6% hydrogen peroxide solution. The obtained ready-to-use hair coloring agent is applied to bleached hair locks and distributed uniformly using a brush. After an action period of 20 minutes at 40° C., the hair is rinsed with lukewarm water, washed with shampoo, rinsed again with lukewarm water, and then dried.

An intensive red-violet dyed lock is obtained.

Example 6

Hair Coloring Agent

| | |
|---|---|
| (1E)-1-{[5-amino-1-(2-hydroxyethyl)-1H-pyrazol-4-yl]imino}-3-[4-(methyloxy)phenyl]-1H-indolizinium-acetate (dye having formula (III) with R1' = 4-methoxyphenyl, R3' = hydrogen, Y = acetate | 1.0 g |
| Ethanol | 30 g |
| Laureth-4 | 0.5 g |
| Water, completely desalinated | balance to 100.0 g |

The pH value is set to 9 with 25% ammonia.

5 g of the above color vehicle is mixed with 5 g of a cationic conditioner (pH=6) and applied to bleached hair locks and distributed uniformly using a brush. After an action period of 20 minutes at 40° C., the hair is rinsed with lukewarm water, washed with a shampoo, rinsed again with lukewarm water, and then dried.

A deep red-violet dyed lock is obtained.

Example 7

Hair Coloring Agent

| | |
|---|---|
| (1E)-1-[(1,5-dimethyl-3-oxo-2-phenyl-2,3-dihydro-1H-pyrazol-4-yl)imino]-3-[4-(methyloxy)phenyl]-1H-indolizinium-acetate (dye having formula (VII) with R1' = 4-methoxyphenyl, R3' = hydrogen, Y = acetate) | 1.0 g |
| Ethanol | 30.0 g |
| Laureth-4 | 0.5 g |
| Water, completely desalinated | balance to 100.0 g |

The pH value is set to 10 with 25% ammonia.

5 g of the above color vehicle is mixed with 5 g of a conditioner. The obtained ready-to-use hair coloring agent is applied to bleached hair locks and is distributed uniformly using a brush. After an action period of 20 minutes at 40° C., the hair is rinsed with lukewarm water, washed with a shampoo, rinsed again with lukewarm water, and then dried.

An intensive red dyed lock is obtained.

Example 8

Hair Coloring Agent

| | |
|---|---|
| (1E)-3-[4-(methyloxy)phenyl]-1-({3-[4-(methyloxy)phenyl]-1-indolizinyl}imino)-1H-indolizinium-acetate (dye having formula (II), with R2 = R2' = hydrogen, R3 = R3' = hydrogen, X = X' = 4-methoxy Y = acetate) | 1.0 g |
| Ethanol | 30.0 g |
| Laureth-4 | 0.5 g |
| Ammonium persulfate | 5.0 g |
| Water, completely desalinated | balance to 100.0 g |

The pH value is set to 10 with 25% ammonia.

5 g of the above color vehicle is mixed with 5 g of a 6% hydrogen peroxide solution. The obtained ready-to-use hair coloring agent is applied to light brown hair locks and is distributed uniformly using a brush. After an action period of 20 minutes at 40° C., the hair is rinsed with lukewarm water, washed with a shampoo, rinsed again with lukewarm water, and then dried. A deep blue-green dyed lock is obtained.

Example 9

Oxidative Hair Colorant (Multi-Component Kit)

Dye pellets manufactured using the top spray method (component A)

| | |
|---|---|
| 3.86 g | 2,4-diamino-phenoxyethanol * HCl |
| 4.71 g | N,N-bis(2-hydroxyethyl)-p-phenylendiamin sulfate |
| 1.00 g | (1E)-1-[(1-Ethyl-5-hydroxy-1H-pyrazol-4-yl)imino]-3-[4-(methyloxy)phenyl]-1H-indolizinium-acetate |
| 3.00 g | ascorbic acid |
| 1.00 g | disodium-ethylendiaminoteraacetate |
| 50.00 g | gum arabic, 20% aqueous solution |

When manufacturing dye pellets in the "top spray" method in a smooth fluidized bed granulator and coater, 6.43 g of filling material (hydrogenated saccharides=mixture of 6-O-α-glucopyranolyl-D-sorbitol and 1-O-α-glucopyranolyl-D-mannitol) is put into place and is heated to a product temperature of about 34° C. at a supplied air temperature of 75° C. and air quantity of 55 m$^3$/h to 65 m$^3$/h. Subsequently, the above aqueous dye dispersion ("spray solution") is sprayed onto the filling material with an initial spray rate of 15 g/min to 22 g/min and a spray air pressure of 1.2 bar to 1.4 bar. In the course of the granulation process, the spray rate and the supplied air temperature are kept constant. Depending on the dye mixture, the air quantity is increased to a maximum of 100 m$^3$/h. Depending on the dye mixture, the product temperature is held between 40° C. and 60° C. during the entire process. After the application of the dye dispersion, the pellets are dried at a maximum product temperature of 60° C., and are subsequently allowed to cool to about 30° C. and are sieved.

Cream Base (Component B)

| | |
|---|---|
| 8.70 g | cetylstearyl alcohol |
| 2.30 g | glycerylstearate (self-emulsifying) |
| 0.80 g | lanolin |
| 3.80 g | lanolin alcohol |
| 1.42 g | steareth-20 |
| 0.07 g | formaldehyde |
| 0.01 g | tocopherol |
| 0.20 g | perfume |
| 10.00 g | ammonia |
| balance to 100.00 g | water |

Oxidizing Agent (Component C)

| | |
|---|---|
| 9.00 g | hydrogen peroxide |
| 1.80 g | cetylstearyl alcohol |
| 3.30 g | polyvinylpyrrolidon/styrene copolymer |
| 0.20 g | disodium phosphate |
| 0.20 g | steareth-20 |
| 0.10 g | salicylic acid |
| 0.08 g | phosphoric acid |
| balance to 100.00 g | water |

Immediately before use, 6 g of the hydrogen peroxide emulsion (component C) is mixed with 6 g of the cream base (component B) and 0.6 g dye pellets (component A) in a dye basin or agitation bottle. The obtained ready-to-use hair coloring agent is applied to light brown locks of hair and is uniformly distributed using a brush. After an action period of 20 minutes at 40° C., the hair is rinsed with lukewarm water, washed with a shampoo, rinsed again with lukewarm water, and then dried.

A deep blue dyed lock is obtained.

Unless indicated otherwise, all percent indications in the present application represent weight percents.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An agent for the oxidative dyeing of fibers, comprising at least one oxidizing agent and at least one cationic azacyanine dye having the general formula (I);

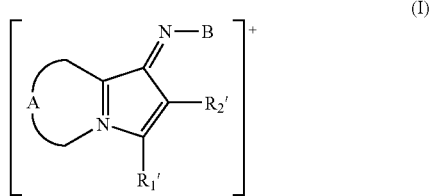

A standing for the 5-or 6-ring group required for the formation of an aromatic carbocyclic or heterocyclic (nitrogen, oxygen or sulfur, up to two additional heteroatoms possibly being contained in addition to the bridge nitrogen);

R1' being equal to an unbranched or branched (C1-C10) alkyl chain that can be selected from the group consisting of one or more alkoxy groups, hydroxyl groups, carboxylic acid amide groups, dialkylamino groups, alkylamino groups, carboxylic acid ester groups, carboxylic acid groups or sulfonic acid groups, an unsubstituted benzyl group, a benzyl group substituted with one or more alkyl groups, alkoxy groups, alkoxyalkyl groups, hydroxyl groups, hydroxyalkyl groups, carboxylic acid amide groups, dialkylamine groups, carboxylic acid ester groups, alkylcarboxylic acid ester groups, carboxylic acid groups, alkylcarboxylic acid groups, sulfonic acid groups or halogen atoms, or with a six-member or five-member aromatic carbocyclic or heterocyclic (nitrogen, oxygen or sulfur) ring that can be unsubstituted or substituted with one or more alkyl groups, alkoxy groups, alkoxyalkyl groups, hydroxyl groups, hydroxyalkyl groups, carboxylic acid amide groups, dialkylamine groups, carboxylic acid ester groups, alkylcarboxylic acid ester groups, carboxylic acid groups alkylcarboxylic acid groups, sulfonic acid groups and halogen atoms;

R2' is selected from the group consisting of hydrogen, an alkyl group, a hydroxyalkyl group, an alkoxyalkyl group, an alkoxy group, a halogen atom, or a six-member or five-member aromatic carbocyclic or heterocyclic (nitrogen, oxygen or sulfur) ring that can be unsubstituted or substituted with an alkyl group, an alkoxy group, an alkoxyalkyl group, a hydroxyl group, a hydroxyalkyl group, an alkylcarboxylic acid amide group, a dialkylamino group, a carboxylic acid ester group, an alkylcarboxylic acid ester group a carboxylic acid group, an alkylcarboxylic acid group, a sulfonic acid group, an alkylsulfonic acid group, an unsubstituted or substituted benzyl group and a halogen atom; and B is an aromatic molecule part with tertiary nitrogen.

2. An agent for simultaneous lightening and dyeing of fibers, comprising at least one oxidizing agent comprising at least one cationic azacyanine dye having the general formula (I) according to claim 1 that is stable in relation to oxidizing agents.

3. An oxidative coloring agent for dyeing fibers on the basis of at least one oxidative dye precursor comprising at least one cationic azacyanine dye having the general formula (I) according to claim 1 that is stable in relation to oxidizing agents.

4. An agent according to claim 2 wherein the oxidizing agent is selected from the group consisting of hydrogen peroxide or its additive compounds, urea, melamine, sodium borate, and sodium carbonate.

5. An agent according to claim 3 wherein the oxidizing agent is selected from the group consisting of hydrogen peroxide or its additive compounds, urea, melamine, sodium borate, and sodium carbonate and persulfates.

6. An agent according to claim 1 wherein the compound of formula (I) is selected from the group consisting of compounds having formulas (Ia) to (Ie), the residues R1', R2', and B having the meaning cited in claim 1, and R3' being equal to hydrogen, an alkyl group, an alkoxy group, an alkoxyalkyl group, a hydroxyl group, a hydroxyalkyl group, an alkylcarboxylic acid amide group, an amino group, an alkylamino group, a dialkylamino group, a carboxylic acid ester group, an alkylcarboxylic acid ester group, a carboxylic acid group, an alkylcarboxylic acid group, a sulfonic acid group, an alkylsulfonic acid group and a halogen atom;

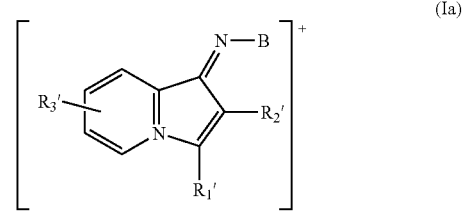

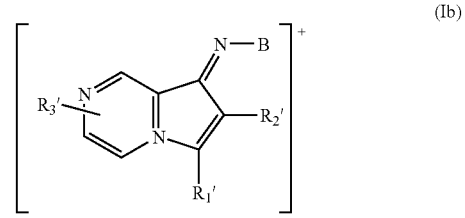

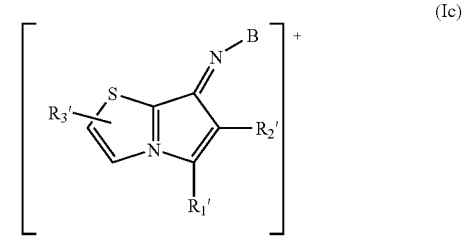

-continued

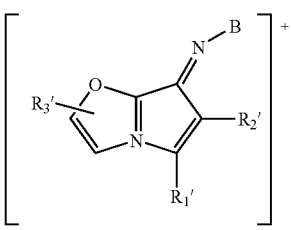
(Id)

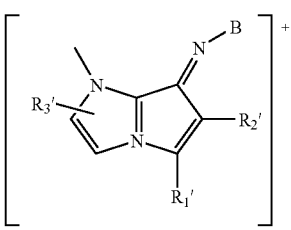
(Ie)

7. An agent according to claim 1 wherein the group B is selected from the group consisting of substituted indoles, indazoles, indolizines, pyrrolo [1,2-a]pyrazinen, pyrrolo[2,1-b][1,3]thiazoles, pyrrolo[2,1-b][1,3]oxazoles, pyrrolol[1,2-a]imidazoles, pyrazoles, paraphenylenamines, imidazoles, pyrroles and pyrazolin-5-ones having formulas (If) to (Ir);

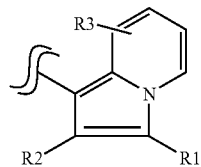
(If)

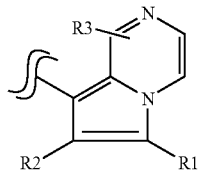
(Ig)

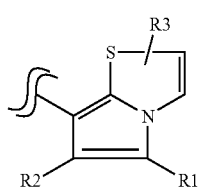
(Ih)

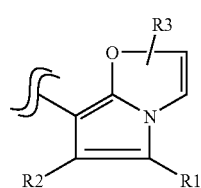
(Ii)

-continued

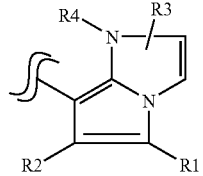
(Ik)

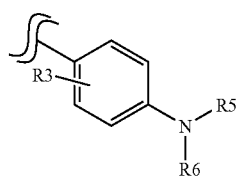
(Il)

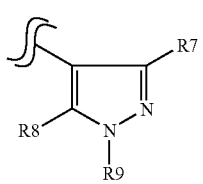
(Im)

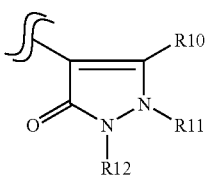
(In)

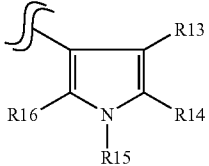
(Io)

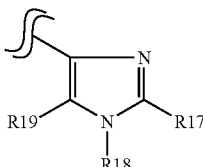
(Ip)

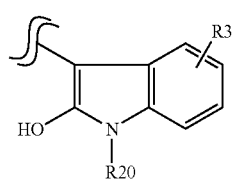
(Iq)

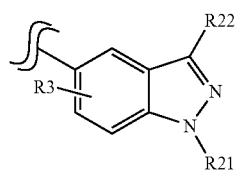
(Ir)

R1 being equal to an unbranched or branched (C1-C10) alkyl chain that can be substituted with one or more alkoxy groups, hydroxyl groups, carboxylic acid amide groups, dialkylamino groups, alkylamino groups, carboxylic acid ester groups, carboxylic acid groups or sulfonic acid groups, an unsubstituted benzyl group, a benzyl group substituted with alkyl groups, alkoxy groups, alkoxyalkyl groups, hydroxyl groups, hydroxyalkyl groups, carboxylic acid amide groups, dialkylamine groups, carboxylic acid ester groups, alkylcarboxylic acid ester groups, carboxylic acid groups, alkylcarboxylic acid groups, sulfonic acid groups or halogen atoms (F, Cl , Br,I) or with a six-member or five-member aromatic carbocyclic or heterocyclic (nitrogen, oxygen or sulfur) ring that can be unsubstituted or substituted with one or more alkyl groups, alkoxy groups, alkoxyalkyl groups, hydroxyl groups, hydroxyalkyl groups, carboxylic acid amide groups, dialkylamine groups, carboxylic acid ester groups, alkylcarboxylic acid ester groups, carboxylic acid groups, alkylcarboxylic acid groups, sulfonic acid groups or halogen atoms (F, Cl , Br, I): and R2 is hydrogen, an alkyl group, a hydroxyalkyl group, an alkoxyalkyl group, an alkoxy group, a halogen atom (F, Cl , Br, I), or a six-member or five-member aromatic carbocyclic or heterocyclic (nitrogen, oxygen or sulfur) ring that can be unsubstituted or substituted with an alkyl group, an alkoxy group, an alkoxy alkyl group, a hydroxyl group, a hydroxyalkyl group, an alkylcarboxylic acid amide group, a dialkylamino group, a carboxylic acid ester group, an alkylcarboxylic acid ester group, a carboxylic acid group, an alkylcarboxylic acid group, a sulfonic acid group, an alkylsulfonic acid group, an unsubstituted or substituted benzyl group or a halogen atom (F, Cl , Br, I);

R3 being equal to hydrogen, an alkyl group, an alkoxy group, an alkoxyalkyl group, a hydroxyl group, a hydroxyalkyl group, an alkylcarboxylic acid amide group, an amino group, an alkylamino group, a dialkylamino group, a carboxylic acid ester group, an alkylcarboxylic acid ester group, a carboxylic acid group, an alkylcarboxylic acid group, a sulfonic acid group, an alkylsulfonic acid group, or a halogen atom; the residues R4, R5, R6, R9, R11, R12, R15, R18, R20 and R21 being, independent of one another, equal to an unbranched or branched (C1-C10) alkyl chain that can be unsubstituted or substituted with an alkoxy group, a hydroxyl group, a carboxylic acid amide group, a dialkylamino group, an alkylamino group, a carboxylic acid ester group, a carboxylic acid group or a sulfonic acid group, an unsubstituted benzyl group, a benzyl group substituted with an alkyl group, an alkoxy group, an alkoxyalkyl group, a hydroxyl group, a hydroxyalkyl group, a carboxylic acid amide group, a dialkylamino group, a carboxylic acid ester group, an alkylcarboxylic acid ester group, a carboxylic acid group, an alkylcarboxylic acid group, a sulfonic acid group or a halogen atom, or with a six-member or five-member aromatic carbocyclic or heterocyclic (nitrogen, oxygen or sulfur) ring that can be unsubstituted or substituted with an alkyl group, an alkoxy group, an alkoxyalkyl group, a hydroxyl group, a hydroxyalkyl group, a carboxylic acid amide group, a dialkylamino group, a carboxylic acid ester group, an alkylcarboxylic acid ester group, a carboxylic acid group, an alkylcarboxylic acid group, a sulfonic acid group or a halogen atom; and R7, R8, R10, R13, R14, R16, R17, R19 and R22 being, independent from one another, equal to hydrogen, an unbranched or branched (C1-C10) alkyl chain that can be unsubstituted or substituted with an alkoxy group, a hydroxyl group, a carboxylic acid amide group, a dialkylamine group, an alkylamine group, a carboxylic acid ester group, a carboxylic acid group or a sulfonic acid group, an unsubstituted benzyl group, a benzyl group substituted with an alkyl group, an alkoxy group, an alkoxyalkyl group, a hydroxyl group, a hydroxyalkyl group, a carboxylic acid amide group, a dialkylamino group, a carboxylic acid ester group, an alkylcarboxylic acid ester group, a carboxylic acid group, an alkylcarboxylic acid group, a sulfonic acid group, or a halogen atom, a hydroxyl group, an amino group, an alkoxy group, a substituted phenyloxy group, a dialkylamino group, a substituted benzylamino group, a substituted phenylamino group, an alkylamino group, or with a six-member or five-member aromatic carbocyclic or heterocyclic (nitrogen, oxygen or sulfur) ring that can be unsubstituted or substituted with an alkyl group, an alkoxy group, an alkoxyalkyl group, a hydroxyl group, a hydroxyalkyl group, a carboxylic acid amide group, a dialkylamine group, a carboxylic acid ester group, an alkylcarboxylic acid ester group, a carboxylic acid group, an alkylcarboxylic acid group, a sulfonic acid group, and a halogen atom.

8. An agent according to claim 1 wherein the azacyanine dye having formula (I) is selected from the group consisting of (1E)-1-({4-[bis(2-hydroxyethyl)amino]phenyl}imino)-3-(4-methoxyphenyl)-2-methyl-1H-indolizinium-acetate, (1E)-1-{[4-(dimethylamino)phenyl]imino}-3-(4-methoxyphenyl)-2-methyl-1H-indolizinium-acetate, (1E)-1-{[4-(diethylamino)phenyl]imino}-3-(4-methoxyphenyl)-2-methyl-1H-indolizinium-acetate, (1E)-1-[(5-amino-1-methyl-1H-pyrazol-4-yl)imino]-3-(4-methoxyphenyl)-2-methyl-1H-indolizinium-acetate, (1E)-1-{[5-amino-1-(4-methylbenzyl)-1H-pyrazol-4-yl]imino}-3-(4-methoxyphenyl)-2-methyl-1H-indolizinium-acetate, (1E)-1-{[5-amino-1-(3-methylbenzyl)-1H-pyrazol-4-yl]imino}-3-(4-methoxyphenyl)-2-methyl-1H-indolizinium-acetate, (1E)-1-{[5-amino-1-(4-methylbenzyl)-1H-pyrazol-4-yl]imino}-3-(4-methoxyphenyl)-2-methyl-1H-indolizinium-acetate, (1E)-1-{[5-amino-1-(2-hydroxymethyl)-1H-pyrazol-4-yl]imino}-3-(4-methoxyphenyl)-2-methyl-1H-indolizinium -acetate, (1E)-1-[(5-amino-1-benzyl-1H-pyrazol-4-yl)imino]-3-(4-methoxyphenyl)-2-methyl-1H-indolizinium-acetate, (1E)-1-[(5-amino-1-ethyl-1H-pyrazol-4-yl)imino]-3-(4-methoxyphenyl)-2-methyl-1H-indolizinium-acetate, (1E)-1-[(5-amino-1-isopropyl-1H-pyrazol-4-yl)imino]-3-(4-methoxyphenyl)-2-methyl-1H-indolizinium-acetate, (1E)-1-[(5-amino-1-pentyl-1H-pyrazol-4-yl)imino]-3-(4-methoxyphenyl)-2-methyl-1H-indolizinium-acetate, (1E)-1-{[5-amino-1-(4-methoxybenzyl)-1H-pyrazol-4-yl]imino}-3-(4-methoxyphenyl)-2-methyl-1H-indolizinium-acetate, (1E)-1-{[(5-amino-1-(3-methoxybenzyl)-1H-pyrazol-4-yl]imino}-3-(4-methoxyphenyl)-2-methyl-1H-indolizinium-acetate, (1E)-1-{[5-amino-1-(2-methoxybenzyl)-1H-pyrazol-4-yl]imino}-3-(4-methoxyphenyl)-2-methyl-1H-indolizinium-acetate, (1E)-1-{[5-amino-1-(4-chlorbenzyl)-1H-pyrazol-4-yl]imino}-3-(4-methoxyphenyl)-2-methyl-1H-indolizinium-acetate, (1E)-1-{[5-amino-1-(3-chlorbenzyl)-1H-pyrazol-4-yl]imino}-3-(4-methoxyphenyl)-2-methyl-1H-indolizinium-acetate, (1E)-1-{[5-amino-1-(2-chlorbenzyl)-1H-pyrazol-4-yl]imino}-3-(4-methoxyphenyl)-2-methyl-1H-indolizinium-acetate, (1E)-1-{[1-(4-methoxybenzyl)-5-(methylamino)-1H-pyrazol-4-yl]imino}-3-(4-methoxyphenyl)-2-methyl-1H-indolizinium-acetate, (1E)-1-{[5-[(2-hydroxyethyl)amino]-1-(4-methoxybenzyl)-1H-pyrazol-4-yl]imino}-3-(4-methoxyphenyl)-2-methyl-1H-indolizinium-acetate, (1E)-1-{[1-(2-hydroxyethyl)-5-methylamino)-1H-pyrazol-4-yl]imino}-3-(4-methoxyphenyl)-2-methyl-1H-indolizinium-acetate, (1E)-1-[(1-ethyl-5-hydroxy-1H-pyrazol-4-yl)imino]-3-(4-methoxyphenyl)-2-methyl-1H-indolizinium-acetate, (1E)-3-(4-methoxyphenyl)-2-methyl-1-[(1-methyl-3-oxo-2-phenyl-2,3-dihydro-1H-pyrazol-4-yl)imino]-1H-indolizinium-acetate, (1E)-1-[(2-hydroxy-4,5-dimethyl-1-phenyl-1H-pyrrol-3-yl)imino]-3-(4-methoxyphenyl)-2-methyl-1H-indolizinium-acetate, (1E)-1-[(5-hydroxy-2-methyl-1-phenyl-1H-imidazol-4-yl)imino]-3-(4-methoxyphenyl)-2-methyl-1H-indolizinium-acetate, (1E)-1-[(2-hydroxy-1-methyl-1H-indol-3-yl)imino]-2-methyl-3-phenyl-1H-indolizinium-acetate, (1E)-1-[(2-hydroxy-1-ethyl-1H-indol-3-yl)imino]-2-methyl-3-phenyl-1H-indolizinium-acetate, (1E)-1-{[2-hydroxy-1-(2-hydroxyethyl)-1H-indol-3-yl]imino}-2-methyl-3-phenyl-1H-indolizinium-acetate, (1E)-3-(4-methoxyphenyl)-1-{[3-(4-methoxyphenyl)-1-indolizinyl]imino}-1H-indolizinium-chloride, (1E)-3-(4-methoxyphenyl)-1-{[3-(4-methoxyphenyl)-1-indolizinyl]imino}-1H-indolizinium-bromide, (8E)-6-(4-methoxyphenyl)-8-{[6-(4-methoxyphenyl)pyrrolo[1,2-a]pyrazin-8-yl]imino}-8H-pyrrolo[1,2-a]pyrazin-5-ium-bromide, (7E)-5-(4-methoxyphenyl)-7-{[5-(4-methoxyphenyl)pyrrolo[2,1-b][1,3]thiazol-7-yl]imino}-7H-pyrrolo[2,1-b][1,3]thiazol-4-ium-chloride, (1E)-3-(4-methoxyphenyl)-1-{[3-(4-methoxyphenyl)-2-methyl-1-indolizinyl]imino}-2-methyl-1H-indolizinium-acetate, (1E)-3-(4-methoxyphenyl)-1-{[3-(4-methoxyphenyl)-2-phenyl-1-indolizinyl]imino}-2-phenyl-1H-indolizinium-acetate, (1E)-1-{[5-amino-1-(2-hydroxyethyl)-1H-pyrazol-4-yl]imino}-3-(4-methoxyphenyl)-2-methyl-1H-indolizinium-acetate, (1E)-1-{[5-amino-1-(2-hydroxyethyl)-1H-pyrazol-4-yl]imino}-2-methyl-3-phenyl-1H-indolizinium-acetate, (1E)-1-{[5-amino-1-(2-hydroxyethyl)-1H-pyrazol-4-yl]imino}-2,3-diphenyl-1H-indolizinium-acetate, (1E)-1-{[-5-(dimethylamino)-1,3-dimethyl-1H-pyrazol-4-yl]imino}-3-(4-methoxyphenyl)-1H-indolizinium-acetate, (1E)-1-{[5-(dimethylamino)-1-(2-hydroxyethyl)-1H-pyrazol-4-yl]imino}-3-(4-methoxyphenyl)-2-methyl-1H-indolizinium-acetate, (1E)-1-{[5-(dimethylamino)-1-(2-hydroxyethyl)-1H-pyrazol-4-yl]imino}-3-(4-methoxyphenyl)-2-phenyl-1H-indolizinium-acetate, (8E)-8-{[5-(dimethylamino)-1-(2-hydroxyethyl)-1H-pyrazol-4-yl]imino}-6-(4-methoxyphenyl)-8H-pyrrolo[1,2-a]pyrazin-5-ium-acetate, (7E)-7-{[5-(dimethylamino)-1-(2-hydroxyethyl)-1H-pyrazol-4-yl]imino}-5-(4-methoxyphenyl)-7H-pyrrolo[2,1-b][1,3]thiazol-4-ium-acetate, (1E)-1-[(1-ethyl-5-hydroxy-1H-pyrazol-4-yl)imino]-2-methyl-3-phenyl-1H-indolizinium-chloride, (1E)-1-[(1-ethyl-5-hydroxy-1H-pyrazol-4-yl)imino]-3-(4-methoxyphenyl)-2-phenyl-1H-indolizinium-chloride, (1E)-1-[(5-hydroxy-1-phenyl-1H-pyrazol-4-yl)imino]-3-(4-methoxyphenyl)-2-phenyl-1H-indolizinium-bromide, (1E)-1-{[5-hydroxy-1-(4-methoxyphenyl)-1H-pyrazol-4-yl]imino}-3-(4-methoxyphenyl)-2-methyl-1H-indolizinium-acetate, (8E)-8-[(1-ethyl-5-hydroxy-1H-pyrazol-4-yl)imino]-6-phenyl-8H-pyrrolo[1,2-a]pyrazin-5-ium-acetate, (7E)-7-[(1-ethyl-5-hydroxy-1H-pyrazol-4-yl)imino]-6-methyl-5-phenyl-7H-pyrrolo[2,1-b][1,3]thiazol-4-ium-chloride, (1E)-1-{[5-(benzylamino)-1-isopropyl-1H-pyrazol-4-yl]imino}-3-phenyl-1H-indolizinium-acetate, (1E)-1-{[5-(benzylamino)-1-isopropyl-1H-pyrazol-4-yl]imino}-2-methyl-3-phenyl-1H-indolizinium-acetate, (7E)-7-{[5-(benzylamino)-1-isopropyl-1H-pyrazol-4-yl]imino}-5-phenyl-7H-pyrrolo[2,1-b][1,3]thiazol-4-ium-acetate, (1E)-1-{[5-(benzylamino)-1-isopropyl-1H-pyrazol-4-yl]imino}-3-(4-hydroxyphenyl)-1H-indolizinium-acetate, (1E)-1-{[5-amino-1-(4-methylbenzyl)-1H-pyrazol-4-yl]imino}-2-methyl-3-phenyl-1H-indolizinium-acetate, (1E)-1-{[5-amino-1-(4-methylbenzyl)-1H-pyrazol-4-yl]imino}-2,7-dimethyl-3-phenyl-1H-indolizinium-acetate, (1E)-1-[(2-hydroxy-1-methyl-1H-indol-3-yl)imino]-2,7-dimethyl-3-phenyl-1H-indolizinium-acetate, (1E)-1-[(1-Ethyl-5-hydroxy-1H-pyrazol-4-yl)imino]-3-[4-(methyloxy)-phenyl]-1H-indolizinium-acetate, (1E)-1-({5-amino-1-[(4-methylphenyl)methyl]-1H-pyrazol-4-yl}imino)-3-[4-(methyloxy)phenyl]-1H-indolizinium-acetate, (1E)-1-({1-(1-methylethyl)-5-[(phenylmethyl)amino]-1H-pyrazol-4-yl}imino)-3-[4-(methyloxy)phenyl]-1H-indolizinium-acetate, (1E)-1-{[5-amino-1-(2-hydroxyethyl)-1H-pyrazol-4-yl]imino}-3-[4-(methyloxy)phenyl]-1H-indolizinium-acetate, (1E)-1-[(1,5-dimethyl-3-oxo-2-phenyl-2,3-dihydro-1H-pyrazol-4-yl)imino]-3-[4-(methyloxy)phenyl]-1H-indolizinium-acetate, (1E)-3-[4-(methyloxy)phenyl[-1-({3-[4-(methyloxy)phenyl]-1-indolizinyl}imino)-1H-indolizinium-acetate and (1E)-1-{[3,5-bis(dimethylamino)-1-methyl-1H-pyrazol-4-yl]imino}-3-(4-methoxyphenyl)-2-methyl-1H-indolizinium acetate.

9. An agent according to claim 1 wherein the azacyanine dye of formula (I) is contained in a total quantity of 0.01wt% to 15wt%.

10. An agent according to claim 1 wherein it additionally comprises natural or synthetic direct-penetrating dyes selected from the group consisting of vegetable dyes, azo dyes, triphenylmethane dyes, quinone dyes, cationic dyes, anionic dyes and nitro dyes.

11. An agent according to claim 1 wherein said agent is a hair dye.

12. A method for dyeing hair having differing degrees of damage, the color vehicle comprising the azacyanine dye having formula (I) according to claim 1 being applied to the previously damaged hair parts without an oxidizing agent in pure form or mixed with an acidic, neutral or basic aqueous thinning agent while the color vehicle mixed with the oxidizing agent is applied to the hair parts that were previously damaged only slightly or not at all.

* * * * *